(12) United States Patent
Shimizu et al.

(10) Patent No.: US 8,173,351 B2
(45) Date of Patent: May 8, 2012

(54) COMPOUND AND RADIATION-SENSITIVE COMPOSITION

(75) Inventors: Daisuke Shimizu, Tokyo (JP); Ken Maruyama, Tokyo (JP); Toshiyuki Kai, Tokyo (JP); Tsutomu Shimokawa, Tokyo (JP)

(73) Assignee: JSR Corporation, Tokyo (JP)

( * ) Notice: Subject to any disclaimer, the term of this patent is extended or adjusted under 35 U.S.C. 154(b) by 312 days.

(21) Appl. No.: 12/519,519

(22) PCT Filed: Jan. 8, 2008

(86) PCT No.: PCT/JP2008/050083
§ 371 (c)(1),
(2), (4) Date: Jun. 16, 2009

(87) PCT Pub. No.: WO2008/084786
PCT Pub. Date: Jul. 17, 2008

(65) Prior Publication Data
US 2009/0274977 A1 Nov. 5, 2009

(30) Foreign Application Priority Data

Jan. 9, 2007 (JP) .................................. 2007-001561
Mar. 5, 2007 (JP) .................................. 2007-054464
Aug. 10, 2007 (JP) .................................. 2007-209882

(51) Int. Cl.
*G03F 7/039* (2006.01)
*G03F 7/004* (2006.01)
*C07C 39/08* (2006.01)
*C07C 39/17* (2006.01)
*C07C 65/01* (2006.01)

(52) U.S. Cl. ..................... 430/270.1; 430/326; 430/914; 430/919; 430/921; 568/720; 568/744; 568/719; 568/721; 568/722; 568/723; 568/729; 568/731; 568/732; 568/733; 562/405; 562/480; 562/488; 562/489; 562/491

(58) Field of Classification Search .................. None
See application file for complete search history.

(56) References Cited

U.S. PATENT DOCUMENTS

| | | | |
|---|---|---|---|
| 5,702,620 | A | 12/1997 | Ohnishi et al. |
| 6,117,617 | A | 9/2000 | Kanayama et al. |
| 6,177,231 | B1 | 1/2001 | Ishii et al. |
| 6,340,553 | B1 | 1/2002 | Oomori et al. |
| 6,395,447 | B1 | 5/2002 | Ishii et al. |
| 6,576,400 | B1 | 6/2003 | Tamura |
| 2007/0123736 | A1 | 5/2007 | Nishikubo et al. |
| 2009/0035691 | A1 | 2/2009 | Shiono et al. |

FOREIGN PATENT DOCUMENTS

| | | |
|---|---|---|
| EP | 1717261 | 11/2006 |
| EP | 1806619 | 7/2007 |
| JP | 07-134413 | 5/1995 |
| JP | 09-211862 | 8/1997 |
| JP | 9-236919 | 9/1997 |
| JP | 10-282649 | 10/1998 |
| JP | 11-029612 | 2/1999 |
| JP | 11-072916 | 3/1999 |
| JP | 11-143074 | 5/1999 |
| JP | 11-258796 | 9/1999 |
| JP | 11-322656 | 11/1999 |
| JP | 2000-147777 | 5/2000 |
| JP | 2006-235340 | 9/2006 |
| JP | 2006-267996 | 10/2006 |
| JP | 2007-008875 | 1/2007 |
| WO | WO 2005/075398 | 8/2005 |

OTHER PUBLICATIONS

DERWENT English abstract for JP 2007-8875 (2007).*
Extended European Search Report for corresponding EP Application No. 08710532.6-1226, Apr. 28, 2011.
Heidi Cao et al., "Sources of Line Width Roughness for EUV Resists", Proceedings of SPIE vol. 5376, pp. 757-764 (SPIE, Bellingham, WA, 2004).
Kadota et al., "Amorphous Molecular Materials: Development of a Novel Positive Electron-beam Molecular Resist", Journal of Photopolymer Science and Technology., vol. 12, No. 2 (1999) pp. 375-376.

* cited by examiner

*Primary Examiner* — Sin J. Lee
(74) *Attorney, Agent, or Firm* — Ditthavong Mori & Steiner, P.C.

(57) ABSTRACT

A compound shown by the following formula (1) can be used as a material for a radiation-sensitive composition capable of forming a resist film which effectively responds to electron beams or the like, exhibits low roughness, and can form a high precision minute pattern in a stable manner.

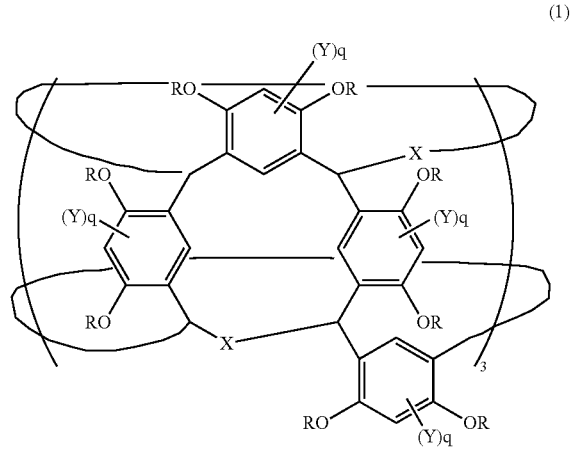

10 Claims, 2 Drawing Sheets

COMPOUND AND RADIATION-SENSITIVE COMPOSITION

TECHNICAL FIELD

The present invention relates to a compound and a radiation-sensitive composition. More particularly, the present invention relates to a compound used as a material for a radiation-sensitive composition capable of forming a chemically-amplified positive-tone resist film which effectively responds to electron beams (hereinafter referred to from time to time as "EB") or extreme ultraviolet radiation (hereinafter referred to from time to time as "EUV"), exhibits low roughness (i.e. a small degree of film surface roughness), excels in etching resistance and sensitivity, and can form high precision minute patterns in a stable manner, and to the radiation-sensitive composition.

BACKGROUND ART

In the field of microfabrication represented by fabrication of integrated circuit devices, manufacture of integrated circuits with a higher degree of integration is demanded. For this reason, downsizing of a design rule using a lithography technology is quickly advancing. That is to say, development of a lithography process which can perform microfabrication in a stable manner is strongly promoted.

In such development of a lithography process, it has become difficult to obtain an integrated circuit with a higher degree of integration, specifically, it is difficult to obtain a more detailed pattern at a higher accuracy as compared with those obtained by a general process using a KrF excimer laser or an ArF excimer laser, for example. For this reason, in recent years, a lithography process using electron beams in place of a KrF excimer laser or an ArF excimer laser has been proposed.

There have been a number of reports disclosing a resist material used for the lithography process using electron beams (electron beam resist material). Examples of such reports include (1) a methacryl main chain cut type positive-tone resist such as polymethyl methacrylate (PMMA) (for example, refer to Patent Documents 1 and 2), (2) a chemically-amplified positive-tone resist containing a polyhydroxystyrene resin partially protected by an acid-dissociable group (resin for a KrF excimer laser), novolak (resin for an i-lines), and an acid generator (for example, refer to Non-patent Document 1), and (3) a positive-tone and negative-tone resist containing an organic low molecule having thin film forming capabilities (amorphous properties) such as calixarene and fullerene (for example, refer to Patent Documents 3 to 11) or a resist using a polyhydric phenol compound (for example, refer to Patent Documents 12 and 13). In addition, a chemically-amplified radiation-sensitive composition containing 1,3,5-tris[4-(2-t-butoxycarbonyloxy)phenyl]benzene as an organic low molecule having thin film forming capabilities other than calixarene and fullerene has also been disclosed (for example, refer to Non-patent Document 2).

[Patent Document 1] JP-A-2000-147777
[Patent Document 2] JP-A-11-29612
[Patent Document 3] JP-A-11-322656
[Patent Document 4] JP-A-11-72916
[Patent Document 5] JP-A-9-236919
[Patent Document 6] WO 2005/075398
[Patent Document 7] JP-A-7-134413
[Patent Document 8] JP-A-9-211862
[Patent Document 9] JP-A-10-282649
[Patent Document 10] JP-A-11-143074
[Patent Document 11] JP-A-11-258796
[Patent Document 12] JP-A-2006-267996
[Patent Document 13] JP-A-2006-235340
[Non-patent Document 1] Proc. SPIE. Vol. 5376, 757-764 (2004)
[Non-patent Document 2] J. Photo Sci. and Tech. Vol. 12, No. 2, 375-376 (1999)

DISCLOSURE OF THE INVENTION

However, among the above-mentioned electron beam resist materials, the methacryl main chain cut type positive-tone resist has problems in etching resistance and sensitivity. It is difficult to use this resist in practice. In order to improve sensitivity, methacryl main chain cut type positive-tone resists modified by, for example, using poly-t-butyl-αchloromethylstyrene (Patent Document 1) or introducing atoms easily cut by electron beams such as N, O, and S into the resin terminals (Patent Document 2) have been proposed. Even though these resins have achieved a certain degree of improvement in sensitivity, none has attained a usable level in practice in both sensitivity and etching resistance. The chemically-amplified positive-tone resist described in Non-patent Document 1 has high sensitivity. However, due to the use of a resin, the resist has a problem of film surface roughness (hereinafter referred to from time to time as "nano edge roughness" or "roughness") when forming minute patterns. The resists using calixarene described in Patent Documents 3 to 5 have excellent etching resistance. However, these resists have very strong interaction between the molecules due to their structure. Their solubility in a developer is poor and it is difficult to obtain satisfactory patterns. Nano edge roughness performance of the compound using calixarene derivatives described in Patent Document 6 is not clear.

Even though the resists using fullerene described in Patent Documents 7 to 11 have excellent etching resistance, their applicability and sensitivity are not at a usable level in practice. In addition, the chemically-amplified resist containing 1,3,5-tris[4-(2-t-butoxycarbonyloxy)phenyl]benzene as an organic low molecule having thin film forming capabilities other than calixarene and fullerene disclosed in Non-patent Document 2 is not sufficient and still to be improved in applicability, adhesion to a substrate, and sensitivity to become usable in practice. The resists using a polyhydric phenol compound described in Patent Documents 12 and 13 exhibit excellent resolution, but their sensitivity is still to be improved to be used in practice.

The present invention has been achieved in view of these problems in general technologies and has an object of providing a compound used as a material for a radiation-sensitive composition capable of forming a chemically-amplified positive-tone resist film which effectively responds to electron beams or extreme ultraviolet radiation, exhibits low roughness, excels in etching resistance and sensitivity, and can form high precision minute patterns in a stable manner, and the radiation-sensitive composition.

As a result of extensive studies in order to achieve the above object, the inventors of the present invention have found that the above object can be achieved by a compound having a specific structure and by a radiation-sensitive composition comprising this compound and a radiation-sensitive acid generator. The finding has led to the completion of the present invention.

According to the present invention, the following compound and radiation-sensitive composition are provided.

[1] A compound shown by the following formula (1),

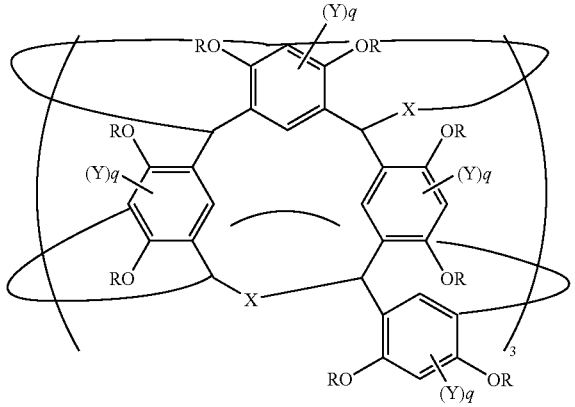

wherein Rs individually represent a hydrogen atom or an acid-dissociable group having a substituted or unsubstituted cyclic structure, provided that at least one of the Rs is an acid-dissociable group having a substituted or unsubstituted cyclic structure; Xs individually represent a substituted or unsubstituted alkylene group having 1 to 8 carbon atoms; Ys individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group; and qs are individually 0 or 1.

[2] The compound according to [1] which is shown by the following formula (2),

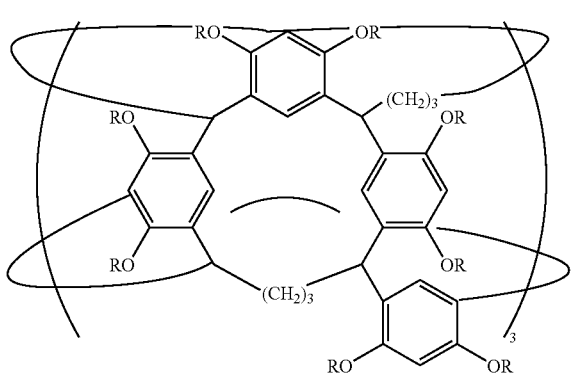

wherein Rs individually represent a hydrogen atom or an acid-dissociable group having a substituted or unsubstituted cyclic structure, provided that at least one of the Rs is an acid-dissociable group having a substituted or unsubstituted cyclic structure.

[3] The compound according to [1] or [2], wherein the acid-dissociable group is shown by the following formula (2-1) or (2-2),

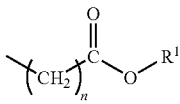

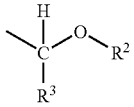

wherein, in the formula (2-1), $R^1$ represents a substituted or unsubstituted cycloalkyl group having 6 to 20 carbon atoms which may contain a hetero atom and n is an integer of 1 to 3, and in the formula (2-2), $R^2$ represents a substituted or unsubstituted cycloalkyl group having 6 to 20 carbon atoms which may contain a hetero atom and $R^3$ represents a hydrogen atom or an alkyl group having 1 to 5 carbon atoms.

[4] The compound according to [3], wherein $R^1$ in the formula (2-1) is a 2-methyl-2-adamantyl group, a 2-ethyl-2-adamantyl group, a 1-ethylcyclopentyl group, or a 1-methylcyclopentyl group, $R^2$ in the formula (2-2) is an adamantyl group, a 2-ethyl-2-adamantyl group, or a 2-methyl-2-adamantyl group, and $R^3$ is a hydrogen atom or a methyl group.

[5] A radiation-sensitive composition comprising (a) a compound according to any one of [1] to [4], and (b) a radiation-sensitive acid generator which generates an acid upon exposure to radiation.

[6] The radiation-sensitive composition according to [5], wherein the radiation-sensitive acid generator (b) is at least one compound selected from the group consisting of an onium salt, a diazomethane compound, and a sulfonimide compound.

[7] The radiation-sensitive composition according to [5] or [6], further comprising (c) an acid diffusion controller.

The compound of the present invention can be used as a material for a radiation-sensitive composition capable of forming a chemically-amplified positive-tone resist film which effectively responds to electron beams or extreme ultraviolet radiation, exhibits low roughness, excels in etching resistance and sensitivity, and can form high precision minute patterns in a stable manner.

Due to inclusion of the compound of the present invention, the composition of the present invention can form a chemically-amplified positive-tone resist film which effectively responds to electron beams or extreme ultraviolet radiation, exhibits low roughness, excels in etching resistance and sensitivity, and can form high precision minute patterns in a stable manner.

EXPLANATION OF SYMBOLS

Figure 1:
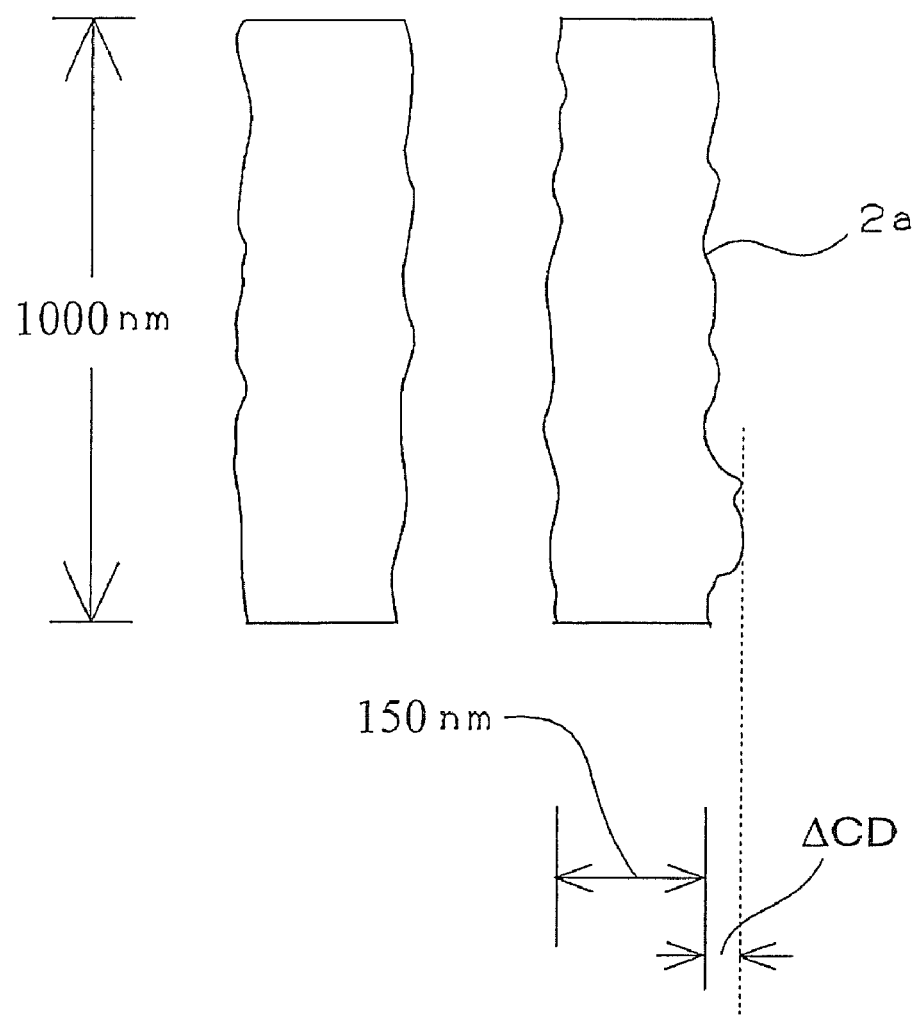
FIG. 1 is a plan view schematically showing a line- and space pattern.

1: silicon wafer, 2: line part, 2a: horizontal side of line part

BEST MODE FOR CARRYING OUT THE INVENTION

Preferred embodiments of the present invention are described below. Note that the present invention is not limited to the following embodiments. Various modifications and improvements may be made in the embodiments without departing from the scope of the present invention based on the knowledge of a person skilled in the art.

[1] Compound:

A compound according to one embodiment of the present invention is shown by the following formula (1) (hereinafter may be referred to from time to time as "compound (a)"). The compound (a) is an acid-dissociable group containing a (modified) compound, in which at least one of the hydroxyl groups is protected by an acid-dissociable group having a substituted or unsubstituted cyclic structure. Therefore, the compound (a) dissociates the acid-dissociable group by the action of an acid and becomes soluble in alkali after dissociation of the acid-dissociable group.

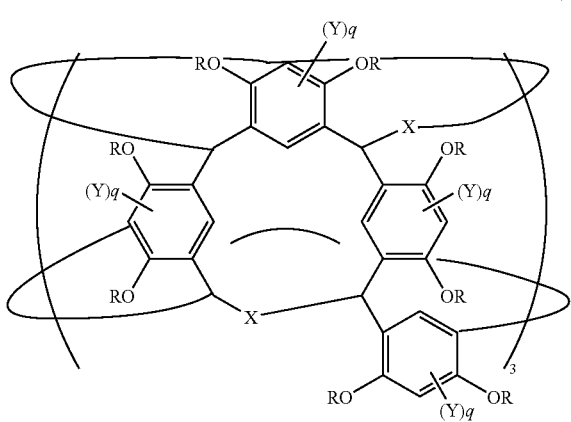

(1)

wherein Rs individually represent a hydrogen atom or an acid-dissociable group having a substituted or unsubstituted cyclic structure, provided that at least one of the Rs is an acid-dissociable group having a substituted or unsubstituted cyclic structure; Xs individually represent a substituted or unsubstituted alkylene group having 1 to 8 carbon atoms; Ys individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group; and qs are individually 0 or 1.

The formula (1) may alternatively shown by the following formula (1-1).

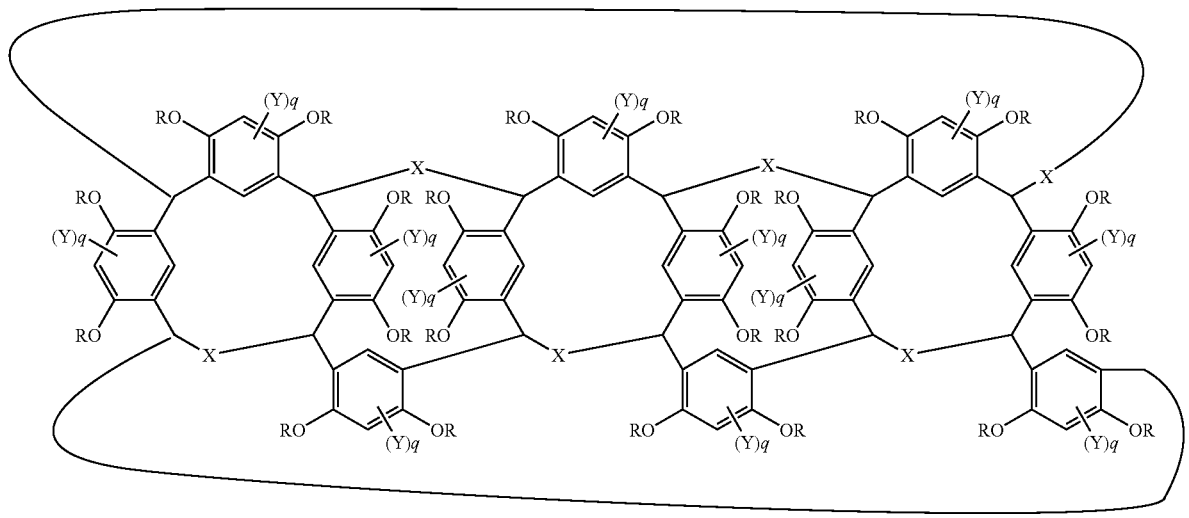

(1-1)

wherein Rs individually represent a hydrogen atom or an acid-dissociable group having a substituted or unsubstituted cyclic structure, provided that at least one of the Rs is an acid-dissociable group having a substituted or unsubstituted cyclic structure; Xs individually represent a substituted or unsubstituted alkylene group having 1 to 8 carbon atoms; Ys individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group; and qs are individually 0 or 1.

As examples of the substituents for the substituted alkyl group having 1 to 10 carbon atoms shown by Y in the formula (1), a methyl group, an ethyl group, a propylene group, and a butylene group can be given. Of these, the propylene group and butylene group are preferable in order to obtain the compound of the embodiment in a high yield.

Among the compounds shown by the formula (1), the compound shown by the following formula (2) is preferable. Specifically, it is preferable that X be a propylene group and q be 0 in the formula (1). Among the compounds shown by the formula (1), the compound shown by the following formula (2) can be produced in a high yield.

(2)

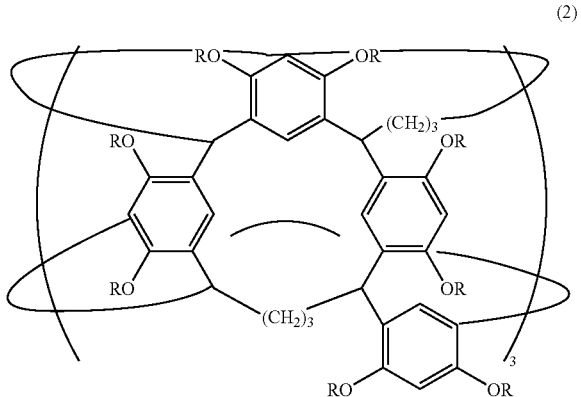

wherein Rs individually represent a hydrogen atom or an acid-dissociable group having a substituted or unsubstituted cyclic structure, provided that at least one of the Rs is an acid-dissociable group having a substituted or unsubstituted cyclic structure.

[1-1] Acid-Dissociable Group:

Rs in the formula (1) individually represent a hydrogen atom or an acid-dissociable group having a substituted or unsubstituted cyclic structure, provided that at least one of the Rs is an acid-dissociable group having a substituted or unsubstituted cyclic structure.

In addition to the requirement that at least one of the Rs in the formula (1) is an acid-dissociable group having a substituted or unsubstituted cyclic structure, it is preferable that at least one of the Rs be a hydrogen atom. If all the Rs in the formula (1) are the acid-dissociable groups, the resist film produced from the radiation-sensitive composition containing the compound of the embodiment has low adhesion to the substrate when patterning is performed, resulting in a tendency for reduced resolution.

Among all the Rs in the compound shown by the formula (1), the proportion of the acid-dissociable group is preferably 10 to 90 mol %, and more preferably 20 to 80 mol %. If the proportion of the acid-dissociable group is less than 10 mol %, resolution tends to decrease. If more than 90 mol %, adhesion of the resist film after patterning to the substrate tends to decrease. The proportion of the acid-dissociable group in the compound shown by the formula (1) is calculated based on the results of $^1$H-NMR analysis.

Although there are no particular limitations to the structure of the acid-dissociable group insofar as the group has a substituted or unsubstituted cyclic structure and is dissociable by the action of an acid, the groups shown by the following formulas (2-1) and (2-2) are preferable. Since Rs in the formula (1) "individually" represent the defined groups, when two or more acid-dissociable groups are present in the formula (1), all Rs may be the group shown by the following formula (2-1) or the group shown by the following formula (2-2), or both the group shown by the following formula (2-1) and the group shown by the following formula (2-2) may be present.

(2-1)

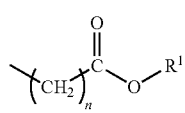

(2-2)

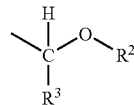

wherein, in the formula (2-1), $R^1$ represents a substituted or unsubstituted cycloalkyl group having 6 to 20 carbon atoms which may contain a hetero atom and n is an integer of 1 to 3, and in the formula (2-2), $R^2$ represents a substituted or unsubstituted cycloalkyl group having 6 to 20 carbon atoms which may contain a hetero atom and $R^3$ represents a hydrogen atom or an alkyl group having 1 to 5 carbon atoms.

As examples of the group shown by the above formula (2-1), the groups shown by the following formulas (3-1) to (3-8) can be given. In the following formulas (3-1) to (3-8), $R^4$ is an alkyl group having 1 to 5 carbon atoms and n is an integer of 1 to 3.

(3-1)

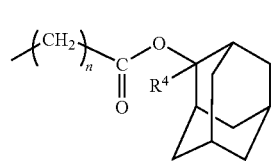

(3-2)

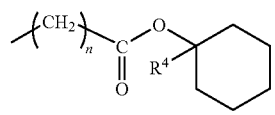

(3-3)

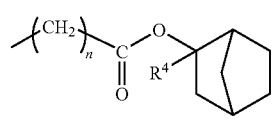

(3-4)

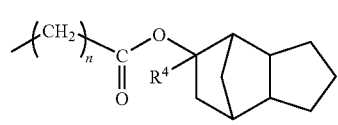

(3-5)

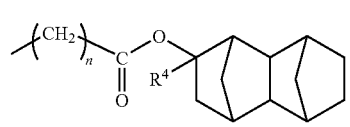

(3-6)

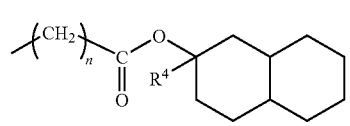

(3-7)

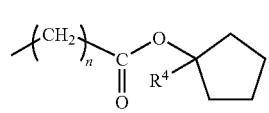

(3-8)

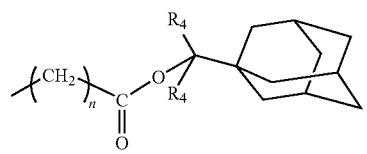

Among the groups shown by the formulas (3-1) to (3-8), the group shown by the formula (3-1), the group shown by the formula (3-7), and the group shown by the formula (3-8) are preferable. When producing the compound (a), among the compounds for introducing the groups shown by the formula (2-1), the compound having the group shown by the formula (3-1), the compound having the group shown by the formula (3-7), and the compound having the group shown by the formula (3-8) have an advantage of easy commercial availability of raw materials.

The group represented by $R^4$ in the above formulas (3-1) to (3-8) is a lower alkyl group (alkyl group having 1 to 5 carbon atoms). As specific examples, linear or branched lower alkyl groups such as a methyl group, an ethyl group, a propyl group, an isopropyl group, an n-butyl group, an isobutyl group, a t-butyl group, a pentyl group, an isopentyl group, and a neopentyl group can be given. Of these, the methyl group or the ethyl group is preferable, with the methyl group being more preferable.

$R^1$ in the formula (2-1) is preferably a 2-methyl-2-adamantyl group, a 2-ethyl-2-adamantyl group, a 1-ethylcyclopentyl group, a 1-methylcyclopentyl group, or a group shown by the following formula (14). When there are two or more groups shown by the formula (2-1), all $R^1$s in the formula (2-1) may be the same groups or each of the $R^1$s may indicate a different group.

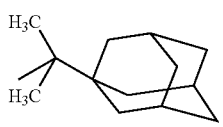

(14)

As the group shown by the formula (2-1), a 2-methyl-2-adamantyloxycarbonylmethyl group, a 2-ethyl-2-adamantyloxycarbonylmethyl group, a 1-ethylcyclopentyloxycarbonylmethyl group, a 1-methylcyclopentyloxycarbonylmethyl group, and a group shown by the following formula (15) are preferable. When two or more groups shown by the formula (2-1) are present, all the groups shown by the formula (2-1) may be the same group or each of such groups may be different from the others.

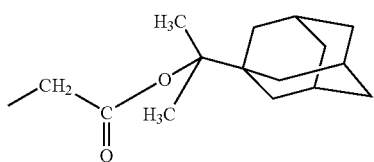

(15)

As examples of the group shown by the above formula (2-2), the groups shown by the following formulas (4-1) to (4-14) can be given. $R^3$ in the following formulas (4-1) to (4-14) is a hydrogen atom or an alkyl group having 1 to 5 carbon atoms, $R^{12}$ in the following formulas (4-1) to (4-10) is a hydrogen atom or an alkyl group having 1 to 5 carbon atoms, m in the following formulas (4-1) to (4-10) is an integer of 0 to 2, and preferably 0 or 1.

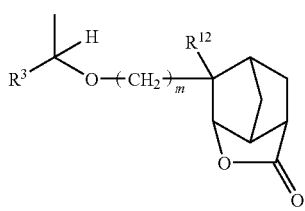

(4-1)

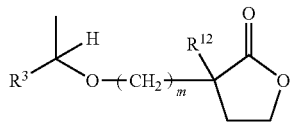

(4-2)

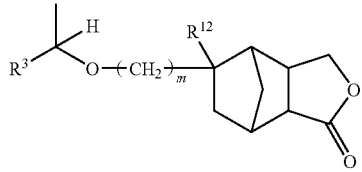

(4-3)

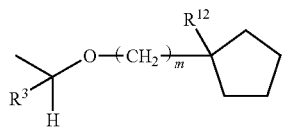

(4-4)

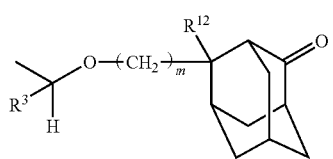

(4-5)

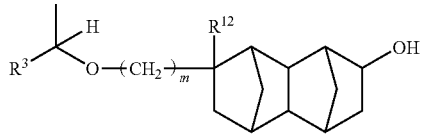

(4-6)

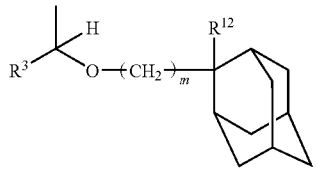

(4-7)

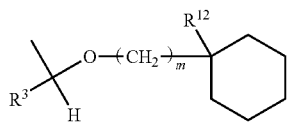

(4-8)

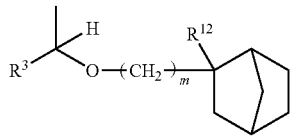

(4-9)

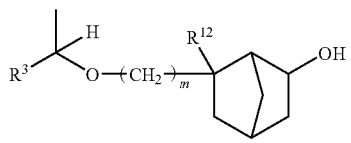

(4-10)

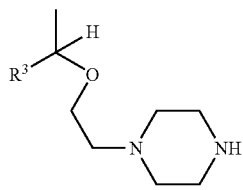

(4-11)

(4-12)

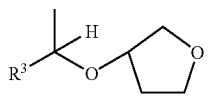

(4-13)

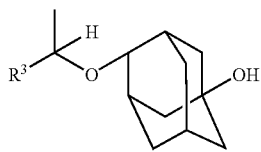

(4-14)

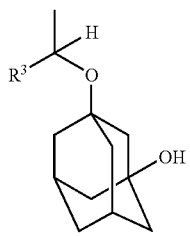

(11)

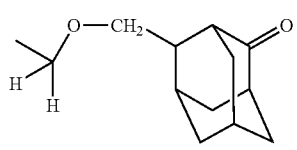

(12)

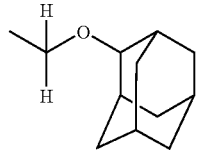

(13)

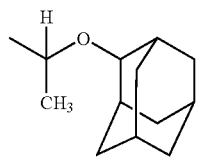

Among the groups shown by the above formula (2-2), the group shown by the formula (4-5) and the group shown by the formula (4-7) are preferable, with the group shown by the formula (4-7) being particularly preferable. When producing the compound (a), among the compounds for introducing the groups shown by the formula (2-2), the compound having the group shown by the formula (4-5) and the compound having the group shown by the formula (4-7) have an advantage of easy commercial availability.

Among the groups shown by the formula (4-7), a 2-adamantyloxymethyl group, a group shown by the following formula (9), a group shown by the following formula (10), a group shown by the following formula (11), a group shown by the following formula (12), and a group shown by the following formula (13) are preferable. When the group shown by the formula (4-7) is the 2-adamantyloxymethyl group, the group shown by the following formula (9), the group shown by the following formula (10), the group shown by the following formula (11), the group shown by the following formula (12), or the group shown by the following formula (13), the resist films produced have improved etching resistance.

(9)

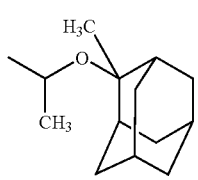

(10)

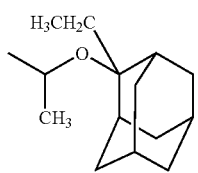

$R^3$ in the above formulas (4-1) to (4-14) and $R^{12}$ in the above formulas (4-1) to (4-10) are individually a hydrogen atom or an alkyl group having 1 to 5 carbon atoms. As the alkyl group having 1 to 5 carbon atoms, linear or branched lower alkyl groups such as a methyl group, an ethyl group, a propyl group, an isopropyl group, an n-butyl group, an isobutyl group, a t-butyl group, a pentyl group, an isopentyl group, and a neopentyl group can be given.

[1-2] Method for Producing the Compound Shown by the Formula (1):

The compound of the embodiment can be obtained by reacting the compound shown by the following formula (1-2) and the compound shown by the following formula (1-3) by a condensation reaction to produce a precursor compound shown by the following formula (1-4), and introducing at least one acid-dissociable group having a substituted or unsubstituted cyclic structure into the precursor compound shown by the following formula (1-4), (1-2)

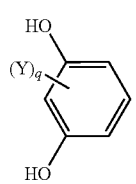

wherein Y individually represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group, and q is 0 or 1,

OHC—X—CHO  (1-3)

wherein X represents a substituted or unsubstituted alkylene group having 1 to 8 carbon atoms, (1-4)

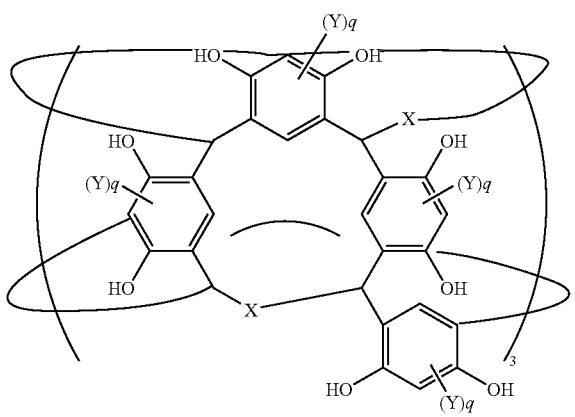

wherein Xs individually represent a substituted or unsubstituted alkylene group having 1 to 8 carbon atoms; Ys individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group; and qs are individually 0 or 1.

There are no particular limitations to the conditions (method) of the condensation reaction. A general method of reacting in the presence of a catalyst such as an acid catalyst at 60 to 90° C. for 12 to 50 hours can be given, for example.

There are no particular limitations to the conditions (method) of introducing the acid-dissociable group. A general method such as a method of reacting the precursor shown by the formula (1-4) with the compound having an acid-dissociable group which has a substituted or unsubstituted cyclic structure in the presence of an acid or a base in a solvent at −20 to 100° C. for 1 to 20 hours can be given.

As preferable examples of the compound having an acid-dissociable group which has a substituted or unsubstituted cyclic structure, the compound having a group shown by the formula (2-1), the compound having a group shown by the formula (2-2), and the like can be given.

As specific examples of the compound having a group shown by the formula (2-1), 2-ethyl-2-adamantyl chloroacetate, 2-ethyl-2-adamantyl bromoacetate, 2-methyl-2-adamantyl chloroacetate, 2-methyl-2-adamantyl bromoacetate, a compound shown by the following formula (16), and a compound shown by the following formula (17) can be given.

(16)

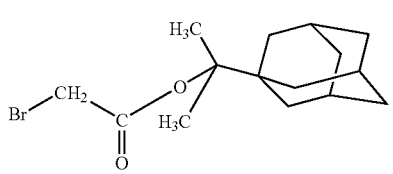

(17)

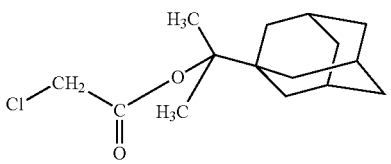

As specific examples of the compound having a group shown by the formula (2-2), 2-adamantyl chloromethyl ether, 2-methyl-2-adamantyl vinyl ether, 2-ethyl-2-adamantyl vinyl ether, and 2-adamantyl vinyl ether can be given.

The amount of the acid-dissociable group to be introduced, that is, the proportion of the acid-dissociable group in all the Rs of the composition shown by the formula (1), may be adjusted by controlling the total amount of the compound having the group shown by the formula (2-1) and the compound having the group shown by the formula (2-2) added to the precursor shown by the formula (1-4).

In producing method of the compound shown by the above formula (2), a compound shown by the following formula (5) and a compound shown by the following formula (6) are reacted at 60 to 90° C. for 12 to 50 hours in a solvent in the presence of a catalyst to effect a dehydration condensation reaction to produce a precursor (a precursor having q=0 in the formula (1-4), hereinafter may be referred to from time to time as "precursor (1-4)"). As the catalyst, an acid catalyst can be given for example.

(5)

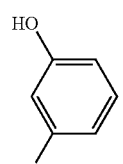

(6)

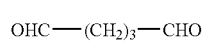

OHC—(CH$_2$)$_3$—CHO

The precursor (1-4) is then reacted with, for example, the compound having a group shown by the formula (2-1), the compound having a group shown by the formula (2-2), or a mixture of these compounds at −20 to 100° C. for 1 to 20 hours in a solvent in the presence of an acid or a base to obtain the compound shown by the formula (2).

Although there are no particular limitations to the mixing ratio (mol ratio) of the compound shown by the above formula (5) (hereinafter may be referred to from time to time as "compound (5)") and the compound shown by the above formula (6) (hereinafter may be referred to from time to time as "compound (6)"), the amount of the compound (5) per one mol of the compound (6) is preferably 1.00 to 8.00 mol, more preferably 2.00 to 6.00 mol, and particularly preferably 3.00 to 5.00 mol from the viewpoint of producing the compound of the embodiment in a high yield. If the mixing ratio of the compound (5) is less than 1.00 mol, the yield of the compound of the embodiment may decrease. If more than 8.00 mol, the yield of the compound of the embodiment may also decrease.

Although the concentration of the substrate (concentration of the total of the compound (5) and compound (6)) in the reaction solution) is not particularly limited, a concentration of 2 mol/l or more is preferable, a concentration of 4 mol/l or more is more preferable, and a concentration of 4 to 10 mol/l is particularly preferable in order to produce the compound of the embodiment in a high yield. If the substrate concentration is less than 2 mol/l, the yield of the resulting compound of the embodiment may decrease.

Although there are no particular limitations to the mixing ratio (mol ratio) of the above precursor (1-4) and the compound having a group shown by the formula (2-1) or the compound having a group shown by the formula (2-2) (the total amount of these compounds when a mixture of these is used), the amount of the compound having a group shown by the formula (2-1) or the compound having a group shown by the formula (2-2) (the total amount of these compounds when a mixture of these is used) per one mol of the precursor (1-4) is preferably one mol or more, more preferably 5 to 40 mol, and particularly preferably 5 to 20 mol in order to ensure a high yield of the compound of the embodiment. If the amount of the compound having a group shown by the formula (2-1) or the compound having a group shown by the formula (2-2) (the total amount of these compounds when a mixture of these is used) is one mol or more, the target compound of the embodiment can be synthesized in a high yield. If less than one mol, the yield of the target compound (the compound of the embodiment) may decrease.

[2] Radiation-Sensitive Composition:

The radiation-sensitive composition in one embodiment of the present invention comprises (a) the compound of the present invention and (b) a radiation-sensitive acid generator which generates an acid upon exposure to radiation. Because of inclusion of the compound (a), the radiation-sensitive composition of the present invention exhibits excellent etching resistance due to the possession of a compound having abenzene ring structure. Since the compound (a) is not a resin, but a low molecular compound, the radiation-sensitive composition is free from aggregation caused by a resin and therefore produces roughness only to a small extent (that is, low roughness). In addition, since the radiation-sensitive composition of the present invention contains a compound having an acid-dissociable group as in a common composition capable of forming a chemically-amplified resist, the composition exhibits high sensitivity. The composition of the present invention thus can form a chemically-amplified positive-tone resist film which effectively responds to electron beams or extreme ultraviolet radiation, exhibits low roughness, excels in etching resistance and sensitivity, and can form high precision minute patterns in a stable manner, when used in a lithography process.

[2-1] (b) Radiation-Sensitive Acid Generator:

The radiation-sensitive acid generator (b) is a component which produces an acid when the radiation-sensitive composition of the present invention is irradiated with electron beams or radioactive rays in a lithography process. The acid-dissociable group in the above-described compound (a) is dissociated by the action of the acid generated from the radiation-sensitive acid generator (b).

As the radiation-sensitive acid generator (b), at least one compound selected from the group consisting of, for example, an onium salt, a diazomethane compound, and a sulfonimide compound is preferable due to excellent acid generating efficiency and heat resistance. These compounds may be used either individually or in combination of two or more.

As examples of the onium salt, iodonium salt, sulfonium salt, phosphonium salt, diazonium salt, and pyridinium salt can be given. As specific examples of the onium salt, triphenylsulfonium trifluoromethanesulfonate, triphenylsulfonium nonafluoro-n-butanesulfonate, triphenylsulfonium benzenesulfonate, triphenylsulfonium 10-camphorsulfonate, triphenylsulfonium n-octanesulfonate, triphenylsulfonium 4-trifluoromethylbenzensulfonate, triphenylsulfonium naphthalenesulfonate, triphenylsulfonium perfluorobenzenesulfonate;

(4-t-butoxyphenyl)diphenylsulfonium trifluoromethanesulfonate, (4-t-butoxyphenyl)diphenylsulfonium nonafluoro-n-butanesulfonate, (4-t-butoxyphenyl)diphenylsulfonium perfluoro-n-octanesulfonate, (4-t-butoxyphenyl)diphenylsulfonium 10-camphorsulfonate, (4-hydroxyphenyl)diphenylsulfonium trifluoromethanesulfonate, (4-hydroxyphenyl)diphenylsulfonium nonafluoro-n-butanesulfonate, (4-hydroxyphenyl)diphenylsulfonium perfluoro-n-octanesulfonate, (4-hydroxyphenyl)diphenylsulfonium 10-camphorsulfonate, (4-hydroxyphenyl)diphenylsulfonium n-octanesulfonate, tris(4-methoxyphenyl)sulfonium trifluoromethanesulfonate, tris(4-methoxyphenyl)sulfonium nonafluoro-n-butanesulfonate, tris(4-methoxyphenyl)sulfonium perfluoro-n-octanesulfonate, tris(4-methoxyphenyl)sulfonium 10-camphorsulfonate, (4-fluorophenyl)diphenylsulfonium trifluoromethanesulfonate, (4-fluorophenyl)diphenylsulfonium nonafluoro-n-butanesulfonate, (4-fluorophenyl)diphenylsulfonium 10-camphorsulfonate; tris(4-fluorophenyl)sulfonium trifluoromethanesulfonate, tris(4-fluorophenyl)sulfonium nonafluoro-n-butanesulfonate, tris(4-fluorophenyl)sulfonium 10-camphorsulfonate, tris(4-fluorophenyl)sulfonium p-toluenesulfonate, tris(4-trifluoromethylphenyl)sulfonium trifluoromethanesulfonate;

2,4,6-trimethylphenyldiphenylsulfonium trifluoromethanesulfonate, 2,4,6-trimethylphenyldiphenylsulfonium 2,4-difluorobenzenesulfonate, 2,4,6-trimethylphenyldiphenylsulfonium 4-trifluoromethylbenzensulfonate; diphenyliodonium trifluoromethanesulfonate, diphenyliodonium nonafluoro-n-butanesulfonate, diphenyliodonium perfluoro-n-octanesulfonate, diphenyliodonium 10-camphorsulfonate, diphenyliodonium n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 10-camphorsulfonate, bis(4-t-butylphenyl)iodonium n-octanesulfonate, (4-methoxyphenyl)phenyliodonium trifluoromethanesulfonate, (4-methoxyphenyl)phenyliodonium nonafluoro-n-butanesulfonate, (4-methoxyphenyl)phenyliodonium perfluoro-n-octanesulfonate, (4-fluorophenyl)phenyliodonium trifluoromethanesulfonate, (4-fluorophenyl)phenyliodonium nonafluoro-n-butanesulfonate, (4-fluorophenyl)phenyliodonium 10-camphorsulfonate; bis(4-fluorophenyl)iodonium trifluoromethanesulfonate, bis(4-fluorophenyl)iodonium nonafluoro-n-butanesulfonate, bis(4-fluorophenyl)iodonium 10-camphorsulfonate;

bis(4-chlorophenyl)iodonium trifluoromethanesulfonate, bis(4-chlorophenyl)iodonium nonafluoro-n-butanesulfonate, bis(4-chlorophenyl)iodonium perfluoro-n-octanesulfonate, bis(4-chlorophenyl)iodonium-n-dodecylbenzenesulfonate, bis(4-chlorophenyl)iodonium 10-camphorsulfonate, bis(4-chlorophenyl)iodonium n-octanesulfonate, bis(4-chlorophenyl)iodonium 4-trifluoromethylbenzensulfonate, bis(4-chlorophenyl)iodonium perfluorobenzenesulfonate;

bis(4-trifluoromethylphenyl)iodonium trifluoromethanesulfonate, bis(4-trifluoromethylphenyl)iodonium nonafluoro-n-butanesulfonate, bis(4-trifluoromethylphenyl)iodonium perfluoro-n-octanesulfonate, bis(4-trifluoromethylphenyl)iodonium n-dodecylbenzenesulfonate, bis(4-trifluoromethylphenyl) iodonium p-toluenesulfonate, bis(4-trifluoromethylphenyl)iodonium benzenesulfonate, bis(4-trifluoromethylphenyl)iodonium 10-camphorsulfonate, bis(4-trifluoromethylphenyl)iodonium n-octanesulfonate, bis(4-trifluoromethylphenyl)iodonium 4-trifluoromethylbenzensulfonate, and bis(4-trifluoromethylphenyl)iodonium perfluorobenzenesulfonate can be given.

Among these, triphenylsulfonium trifluoromethanesulfonate, triphenylsulfonium nonafluoro-n-butanesulfonate, triphenylsulfonium 10-camphorsulfonate, (4-hydroxyphenyl)diphenylsulfonium trifluoromethanesulfonate, (4-hydroxyphenyl)diphenylsulfonium nonafluoro-n-butanesulfonate, tris(4-methoxyphenyl)sulfonium trifluoromethanesulfonate, tris(4-methoxyphenyl)sulfonium nonafluoro-n-butanesulfonate, (4-fluorophenyl)diphenylsulfonium trifluoromethanesulfonate, (4-fluorophenyl)diphenylsulfonium nonafluoro-n-butanesulfonate, 2,4,6-trimethylphenyldiphenylsulfonium trifluoromethanesulfonate, 2,4,6-trimethylphenyldiphenylsulfonium 2,4-difluorobenzenesulfonate, 2,4,6-trimethylphenyldiphenylsulfonium 4-trifluoromethylbenzensulfonate,
diphenyliodonium trifluoromethanesulfonate, diphenyliodonium nonafluoro-n-butanesulfonate, diphenyliodonium 10-camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium 10-camphorsulfonate, (4-fluorophenyl)phenyliodonium trifluoromethanesulfonate, (4-fluorophenyl)phenyliodonium nonafluoro-n-butanesulfonate, (4-fluorophenyl) phenyliodonium 10-camphorsulfonate, bis(4-fluorophenyl)iodonium trifluoromethanesulfonate, bis(4-fluorophenyl)iodonium nonafluoro-n-butanesulfonate, bis (4-fluorophenyl)iodonium 10-camphorsulfonate, and tris (4-trifluoromethylphenyl)sulfonium trifluoromethanesulfonate are preferable. These compounds may be used either individually or in combination of two or more.

As specific examples of the diazomethane compounds, bis(trifluoromethanesulfonyl)diazomethane, bis(cyclohexylsulfonyl)diazomethane, bis(3,3-dimethyl-1,5-dioxaspiro[5.5]dodecane-8-sulfonyl)di azomethane, bis(1,4-dioxaspiro[4.5]decane-7-sulfonyl)diazomethane, bis(t-butylsulfonyl) diazomethane, and the like can be given.

Among these compounds, bis(cyclohexylsulfonyl)diazomethane, bis(3,3-dimethyl-1,5-dioxaspiro[5.5]dodecane-8-sulfonyl)di azomethane, and bis(1,4-dioxaspiro[4.5]decane-7-sulfonyl)diazomethane are preferable. These compounds may be used either individually or in combination of two or more.

Specific examples of sulfonimide compounds include N-(trifluoromethylsulfonyloxy)bicyclo[2.2.1]hept-5-ene-2,3-dicarboxylmide, N-(trifluoromethylsulfonyloxy)-7-oxabicyclo[2.2.1]hept-5-ene-2,3-dicarboxylmide, N-(trifluoromethylsulfonyloxy)bicyclo[2.2.1]heptan-5,6-oxy-2,3-dicarboxylmide; N-(10-camphorsulfonyloxy)succinimide, N-(10-camphorsulfonyloxy)phthalimide, N-(10-camphorsulfonyloxy)-7-oxabicyclo[2.2.1]hept-5-ene-2,3-dicarboxylmide, N-(10-camphorsulfonyloxy)bicyclo[2.2.1]heptan-5,6-oxy-2,3-dicarboxylmide, N-(10-camphorsulfonyloxy) naphthylimide, N-[(5-methyl-5-carboxymethylbicyclo [2.2.1]heptan-2-yl)sulf onyloxy] succinimide; N-(n-octylsulfonyloxy)bicyclo[2.2.1]hept-5-ene-2,3-dicarbo xyimide, N-(n-octylsulfonyloxy)bicyclo[2.2.1]heptan-5,6-oxy-2,3-dic arboxyimide, N-(perfluorophenylsulfonyloxy)bicyclo[2.2.1]hept-5-ene-2,3-dicarboxylmide, N-(perfluorophenylsulfonyloxy)-7-oxabicyclo[2.2.1]hept-5-ene-2,3-dicarboxylmide, N-(perfluorophenylsulfonyloxy)bicyclo[2.2.1]heptan-5,6-oxy-2,3-dicarboxylmide, N-(nonafluoro-n-butylsulfonyloxy)bicyclo[2.2.1]hept-5-ene-2,3-dicarboxylmide, N-(nonafluoro-n-butylsulfonyloxy)-7-oxabicyclo[2.2.1]hept-5-ene-2,3-dicarboxylmide, N-(nonafluoro-n-butylsulfonyloxy)bicyclo[2.2.1]heptan-5,6-oxy-2,3-dicarboxylmide; N-(perfluoro-n-octylsulfonyloxy)bicyclo[2.2.1]hept-5-ene-2,3-dicarboxylmide, N-(perfluoro-n-octylsulfonyloxy)-7-oxabicyclo[2.2.1]hept-5-ene-2,3-dicarboxylmide, and N-(perfluoro-n-octylsulfonyloxy)bicyclo[2.2.1]heptan-5, 6-o xy-2,3-dicarboxylmide.

Among these, N-(trifluoromethylsulfonyloxy)bicyclo [2.2.1]hept-5-ene-2,3-dicarboxylmide, N-(10-camphorsulfonyloxy)succinimide, and N-[(5-methyl-5-carboxymethylbicyclo[2.2.1]heptan-2-yl)sulf onyloxy]succinimide are preferable. These compounds may be used either individually or in combination of two or more.

The radiation-sensitive acid generator (b) is added to the composition in an amount of preferably 0.1 to 20 parts by mass, and more preferably 0.5 to 15 parts by mass for 100 parts by mass of the compound (a). If the amount of the radiation-sensitive acid generator (b) is less than 0.1 part by mass, sensitivity and developability may be impaired. If more than 20 parts by mass, transparency to radioactive rays, the pattern shape, heat resistance, and the like may be impaired.

[2-2] (c) Acid Diffusion Controller:

It is desirable that the radiation-sensitive composition of the present invention further comprise an acid diffusion controller (c). The acid diffusion controller (c) is a component which controls diffusion of an acid generated from the radiation-sensitive acid generator (b) upon exposure in the resist film and suppresses undesired chemical reactions in the unexposed area. The addition of such an acid diffusion controller (c) improves storage stability of the resulting radiation-sensitive composition and resolution of the formed resist film. Moreover, the addition of the acid diffusion controller prevents the line width of the resist pattern from changing due to changes in the post-exposure delay (PED) which is a time between the completion of exposure and the post exposure heat treatment, whereby a radiation-sensitive composition with remarkably superior process stability can be obtained.

Nitrogen-containing organic compounds or photosensitive basic compounds are preferable as the acid diffusion controller (c). As examples of the nitrogen-containing organic compound, compounds shown by the following formula (7) (hereinafter referred to as "nitrogen-containing compounds (i)"), compounds having two nitrogen atoms in the molecule (hereinafter referred to as "nitrogen-containing compounds (ii)"), polyamino compounds or polymers having three or more nitrogen atoms (hereinafter collectively referred to as "nitrogen-containing compounds (iii)"), amide group-containing compounds, urea compounds, nitrogen-containing heterocyclic compounds, and the like can be given.

(7)

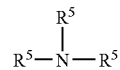

wherein $R^5$ individually represents a hydrogen atom, a substituted or unsubstituted, linear, branched, or cyclic alkyl group, a substituted or unsubstituted aryl group, or a substituted or unsubstituted aralkyl group.

As examples of the nitrogen-containing compound (i), mono(cyclo)alkylamines such as n-hexylamine, n-heptylamine, n-octylamine, n-nonylamine, n-decylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, methyldicyclohexylamine, and tricyclohexylamine; and substitute alkylamines such as triethanolamine; aromatic amines such as aniline, N-methylaniline, N,N-dimethylaniline, 2-methylaniline, 3-methylaniline, 4-methylaniline, 4-nitroaniline, diphenylamine, triphenylamine, naphthylamine, 2,4,6-tri-tert-butyl-N-methylaniline, N-phenyldiethanolamine, and 2,6-diisopropylaniline are preferable.

Examples of the nitrogen-containing compounds (ii) include ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene, bis(2-dimethylaminoethyl)ether, bis(2-diethylaminoethyl)ether, 1-(2-hydroxyethyl)-2-imidazolizinone, 2-quinoxalinol, N,N,N',N'-tetrakis(2-hydroxypropyl)ethylenediamine, and N,N,N',N'',N''-pentamethyldiethylenetriamine.

As examples of the nitrogen-containing compound (iii), polyethyleneimine, polyallylamine, and a polymer of 2-dimethylaminoethylacrylamide are preferable.

As examples of the amide group-containing compounds, N-t-butoxycarbonyl group-containing amino compounds such as N-t-butoxycarbonyldi-n-octylamine, N-t-butoxycarbonyldi-n-nonylamine, N-t-butoxycarbonyldi-n-decylamine, N-t-butoxycarbonyldicyclohexylamine, N-t-butoxycarbonyl-1-adamantylamine, N-t-butoxycarbonyl-2-adamantylamine, N-t-butoxycarbonyl-N-methyl-1-adamantylamine, (S)-(−)-1-(t-butoxycarbonyl)-2-pyrrolidinemethanol, (R)-(+)-1-(t-butoxycarbonyl)-2-pyrrolidinemethanol, N-t-butoxycarbonyl-4-hydroxypiperidine, N-t-butoxycarbonylpyrrolidine, N-t-butoxycarbonylpiperazine, N,N-di-t-butoxycarbonyl-1-adamantylamine, N,N'-di-t-butoxycarbonyl-N-methyl-1-adamantylamine, N-t-butoxycarbonyl-4,4'-diaminodiphenylmethane, N,N'-di-t-butoxycarbonylhexamethylenediamine, N,N,N'N'-tetra-t-butoxycarbonylhexamethylenediamine, N,N'-di-t-butoxycarbonyl-1,7-diaminoheptane, N,N'-di-t-butoxycarbonyl-1,8-diaminonooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole, N-t-butoxycarbonyl-2-phenylbenzimidazole; formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine, tris(2-hydroxyethyl)isocyanuric acid, and the like can be given.

As examples of the preferable urea compounds, urea, methylurea, 1,1-dimethylurea, 1,3-dimethylurea, 1,1,3,3-tetramethylurea, 1,3-diphenylurea, and tri-n-butylthiourea can be given.

Examples of the nitrogen-containing heterocyclic compounds include: imidazoles such as imidazole, 4-methylimidazole, 4-methyl-2-phenylimidazole, benzimidazole, 2-phenylbenzimidazole, 1-benzyl-2-methylimidazole, and 1-benzyl-2-methyl-1H-imidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic acid amide, quinoline, 4-hydroxyquinoline, 8-oxyquinoline, acridine, and 2,2':6',2''-terpyridine; piperazines such as piperazine and 1-(2-hydroxyethyl)piperazine; and pyrazine, pyrazole, pyridazine, quinoxaline, purine, pyrrolidine, piperidine, piperidineethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine, and 1,4-diazabicyclo[2.2.2]octane.

The photosensitive basic compound is a component of which the exposed area is efficiently decomposed into corresponding neutral fragments and the unexposed area remains as is without being decomposed. Since such a photosensitive basic compound can effectively utilize the acid generated in the exposed area, the compound can improve sensitivity more effectively as compared with a non-photosensitive basic compound.

There are no specific limitations to the type of the photosensitive basic compound inasmuch as the compound has the above properties. For example, a compound shown by the following formula (8-1) and a compound shown by the following formula (8-2) can be suitably used.

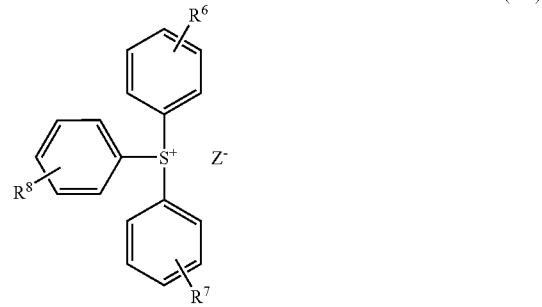

(8-1)

(8-2)

wherein, $R^6$ to $R^{10}$ individually represent a hydrogen atom, a halogen atom, a substituted or unsubstituted alkyl group having 1 to 10 carbon atoms, or a substituted or unsubstituted alicyclic hydrocarbon group and $Z^-$ is $OH^-$, $R^{11}OH^-$, or $R^{11}COO^-$, wherein $R^{11}$ represents a monovalent organic group.

As examples of the substituted or unsubstituted alkyl group having 1 to 10 carbon atoms represented by $R^6$ to $R^{10}$, a methyl group, an ethyl group, an n-butyl group, a t-butyl group, a trifluoromethyl group, a fluorine atom, a methoxy group, a t-butoxy group, and a t-butoxycarbonylmethyloxy group can be given. $R^6$ to $R^{10}$ are preferably hydrogen atoms or t-butyl groups.

As examples of the monovalent organic group represented by $R^{11}$, a substituted or unsubstituted alkyl group and a substituted or unsubstituted aryl group can be given.

As $Z^-$, $OH^-$, $CH_3COO^-$, and compounds shown by the following formulas are preferable.

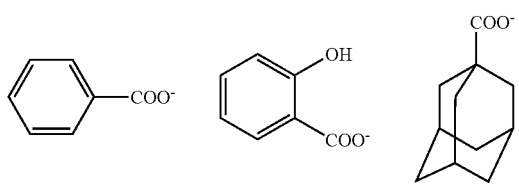

As specific examples of the photosensitive basic compound, a triphenylsulfonium compound (compound shown by the above formula (8-1)) in which the anion moiety ($Z^-$) is $OH^-$, $CH_3COO^-$, or the compound shown by the above formulas can be given.

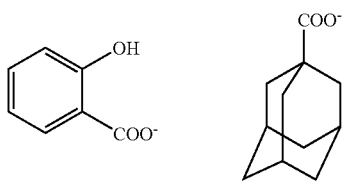

These acid diffusion controllers (c) may be used either individually or in combination of two or more.

The acid diffusion controller (c) is added to the composition in an amount of preferably 15 parts by mass or less, and more preferably 0.001 to 10 parts by mass, and particularly preferably 0.005 to 5 parts by mass for 100 parts by mass of the compound (a). If the amount of the acid diffusion controller (c) exceeds 15 parts by mass, sensitivity of the resulting resist film and developability of the exposed area may be poor. If the amount of the acid diffusion controller (c) is less than 0.001 part by mass, the pattern configuration or dimensional accuracy of the resulting resist film may decrease depending on the processing conditions.

[2-3] Other Components:

It is desirable that the radiation-sensitive composition of the present invention comprise the above-mentioned compound (a), radiation-sensitive acid generator (b), and acid diffusion controller (c) dissolved in a solvent. That is, it is desirable that the composition further comprise a solvent as another component. Various other additives such as surfactants, sensitizers, aliphatic additives, and the like can be optionally added to the radiation-sensitive composition of the present invention.

As the solvent, at least one solvent selected from the group consisting of linear or branched ketones, cyclic ketones, propylene glycol monoalkyl ether acetates, alkyl 2-hydroxypropionates, alkyl 3-alkoxypropionates, and γ-butyrolactone (hereinafter referred to as "solvent 1") is preferable.

The solvent is used in the radiation-sensitive composition of the present invention in an amount to make the total solid content of the composition preferably 5 to 70 mass %, more preferably 10 to 25 mass %, and particularly preferably 10 to 20 mass %.

The radiation-sensitive composition of the present invention has a total solid content of preferably 1 to 50 mass %, and more preferably 1 to 25 mass %. The radiation-sensitive composition of the present invention can be prepared by homogeneously dissolving the compound (a), the radiation-sensitive acid generator (b), the acid diffusion controller (c), and the other optional components (excluding a solvent) in a solvent so as to obtain a total solid content in the above range. The composition thus prepared is preferably filtered through a filter with a pore size of about 0.2 micrometers, for example.

The surfactants used as one of the other additives is a component exhibiting functions of improving applicability, striation, developability, and the like. As examples of the surfactant, nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate; and commercially available products such as "KP341" (manufactured by Shin-Etsu Chemical Co., Ltd.), "POLYFLOW No. 75" and "POLYFLOW No. 95" (manufactured by Kyoeisha Chemical Co., Ltd.), "FTOP EF301", "FTOP EF303", and "FTOP EF352" (manufactured by Tohkem Products Corp.), "MEGAFAC F171" and "MEGAFAC F173" (manufactured by Dainippon Ink and Chemicals, Inc.), "Fluorad FC430" and "Fluorad FC431" (manufactured by Sumitomo 3M Ltd.), "Asahi Guard AG710" and "Surflon S-382", "Surflon SC-101", "Surflon SC-102", "Surflon SC-103", "Surflon SC-104", "Surflon SC-105", and "Surflon SC-106" (manufactured by Asahi Glass Co., Ltd.) can be given. These surfactants may be used either individually or in combination of two or more. The amount of the surfactants is usually 0.001 to 2 parts by mass per 100 parts by mass of the compound (a).

The sensitizers absorb radiation energy and transmit the energy to the radiation-sensitive acid generator (b), thereby increasing the amount of the acid generated upon exposure. The sensitizers improve apparent sensitivity of the radiation-sensitive composition. As examples of the sensitizer, carbazoles, acetophenones, benzophenones, naphthalenes, phenols, biacetyl, Eosine, Rose Bengal, pyrenes, anthracenes, phenothiazines, and the like can be given. These sensitizers may be used either individually or in combination of two or more. The amount of the sensitizers is preferably 0.1 to 10 parts by mass per 100 parts by mass of the compound (a).

Addition of a dye or a pigment visualizes a latent image in the exposed area, thereby decreasing the effects of halation during exposure. Use of an adhesion improver improves adhesion of the resist film to the substrates.

Alicyclic additives having an acid-dissociable group and alicyclic additives having no acid-dissociable group may be added to the radiation-sensitive composition of the present invention. The alicyclic additives having an acid-dissociable group and alicyclic additives having no acid-dissociable group further improve dry etching resistance, pattern shape, and adhesion to the substrate.

As examples of such alicyclic additives, adamantane derivatives such as 1-adamantane carboxylic acid, 2-adamantanone, t-butyl-1-adamantane carboxylic acid, t-butoxycarbonylmethyl 1-adamantanecarboxylate, α-butyrolactone-1-adamantanecarboxylate, di-t-butyl-1,3-adamantanedicarboxylate, t-butyl-1-adamantaneacetate, t-butoxycarbonylmethyl-1-adamantaneacetate, di-t-butyl-1, 3-adamantanediacetate, and 2,5-dimethyl-2,5-di(adamantylcarbonyloxy)hexane; deoxycholates such as t-butyl deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate; lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, and mevalonolactone lithocholate; alkyl carboxylates such as dimethyl adipate, diethyl adipate, dipropyl adipate, di-n-butyl adipate, and di-t-butyl adipate; 3-[2-hydroxy-2,2-bis(trifluoromethyl)ethyl]tetracyclo[4.4.0.1$^{2,5}$.1$^{7,10}$]dodecane and the like can be given.

These alicyclic additives may be used either individually or in combination of two or more. The amount of the alicyclic additives is usually 0.5 to 20 parts by mass per 100 parts by mass of the compound (a). If the amount of the alicyclic additives exceeds 20 parts by mass, heat resistance of the resulting resist film may be poor.

As other additives, low molecular weight alkali solubility controllers containing an alkali-soluble resin and/or acid dissociable protecting group, halation inhibitors, preservation stabilizers, antifoaming agents, and the like can be given.

[3] Process of Resist Pattern Formation:

The radiation-sensitive resin composition of the present invention is useful as a material for forming a chemically-amplified positive-tone resist film. In the chemically-amplified positive-tone resist film, the acid-dissociable group is dissociated by the action of the acid generated from the radiation-sensitive acid generator (b), whereby the compound (a) becomes soluble in alkali. Specifically, alkali soluble sites are produced in the resist film. The alkali soluble sites are the exposed area of the resist which is dissolved and removed by an alkali developer. A positive-tone resist pattern having a desired shape can be formed in this manner. The process of the resist pattern formation is described below in detail.

In order to form a resist pattern using the radiation-sensitive composition of the present invention, a resist film is first produced from the radiation-sensitive composition. As the radiation-sensitive composition, the composition prepared by adjusting the total solid component as mentioned above can be used after filtering through a filter with a pore size of about 0.2 micrometers. A resist film is formed by applying this radiation-sensitive composition to a substrate such as a silicon wafer or a wafer coated with aluminum using an appropriate application method such as rotational coating, cast coating, and roll coating. After that, the coated film may be pre-baked (hereinafter referred to as "PB"). The resist film is then exposed to radiation to obtain a desired resist pattern. As examples of radiation which can be used for the exposure, deep ultraviolet rays such as a KrF excimer laser (wavelength: 248 nm), an EUV (extreme ultraviolet radiation, wavelength: 13 nm), X-rays such as synchrotron radiation, charged particle rays such as electron beams, and the like can be given. The exposure conditions such as radiation dose are appropriately determined according to the composition of the radiation-sensitive composition, types of additives, and the like. Liquid immersion exposure may be used.

It is preferable to perform a post exposure baking (hereinafter referred to as "PEB") after exposure. PEB ensures smooth dissociation of the acid-dissociable group from the compound (a). Although the heating conditions of PEB can be appropriately selected according to the composition of the radiation-sensitive composition, a temperature in a range from 30 to 200° C. is preferable, and from 50 to 170° C. is more preferable.

In order to bring out the potential capability of the radiation-sensitive composition to the maximum extent, an organic or inorganic antireflection film may be formed on the substrate as disclosed in JP-B-6-12452, for example. In addition, a protective film may be provided on the resist film in order to prevent an adverse effect of basic impurities and the like that are present in the environmental atmosphere using a method described in, for example, JP-A-5-188598. These techniques may be used in combination.

The exposed resist film is then developed to form a specified resist pattern. As examples of the developer used, it is preferable to use an alkaline aqueous solution prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, and 1,5-diazabicyclo-[4.3.0]-5-nonene.

The concentration of the alkaline aqueous solution is preferably 10 mass % or less. If the concentration of the alkaline aqueous solution exceeds 10 mass %, an unexposed area may also be dissolved in the developer. The pH of the developer is preferably 8 to 14, and more preferably 9 to 14.

Organic solvents, for example, may be added to the alkaline aqueous solution developer. As examples of the organic solvent, ketones such as acetone, methyl ethyl ketone, methyl i-butyl ketone, cyclopentanone, cyclohexanone, 3-methylcyclopentanone, and 2,6-dimethylcyclohexanone; alcohols such as methylalcohol, ethylalcohol, n-propylalcohol, i-propylalcohol, n-butylalcohol, t-butylalcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol; acetonylacetone; and dimethylformamide can be given. These organic solvents may be used either individually or in combination of two or more.

The amount of the organic solvent to be used is preferably 100 parts by volume or less for 100 parts by volume of the alkaline aqueous solution. The amount of the organic solvent exceeding 100 parts by volume may decrease developability, giving rise to a larger undeveloped portion in the exposed area. In addition, surfactants or the like may be added to the developer containing the alkaline aqueous solution in an appropriate amount. After development using the alkaline aqueous solution developer, the resist film may be washed with water and dried.

EXAMPLES

The present invention is described below in detail by way of examples. Note that the present invention is not limited to the following examples. In the examples, "part(s)" means "part(s) by mass" and "%" means "mass %" unless otherwise indicated.

The following compounds (A-1) to (A-4), (A-8), and (A-9) were synthesized as compound shown by the formula (1) (Compound (a)) and the following compounds (A-5) to (A-7) were synthesized for comparison.

Example 1

Compound (A-1)

In 45 ml of ethanol, 22.0 g (200 mmol) of resorcinol was added and dissolved, and then 15 ml of hydrochloric acid was added. The solution was cooled with ice to 5° C. while stirring and 10.0 g (50 mmol) of 50% aqueous solution of glutaraldehyde was slowly added dropwise. The mixture was heated at 80° C. for 48 hours to obtain a turbid yellow solution. The suspension was poured into methanol, and the resulting precipitate was collected by filtration. The precipitate was washed three times with methanol. The washed precipitate was dried under reduced pressure at room temperature for 24 hours to obtain a powdery light yellow solid (S) (11.2 g (yield: 79%)).

The structure of the resulting light yellow solid (S) was identified using an MALDI-TOF-MS (Model No. SHIMAZU/KRATOS matrix support laser ionization flight time-type mass spectroscope, KOMPACT MALDI IV tDE, manufactured by Shimadzu Corp.), an IR (Model No. FT-IR 420-type, manufactured by Jasco Corp.), and a $^1$H-NMR (Model No. JNM-ECA-500-type manufactured by JEOL Ltd.). The results are shown below.

MALDI-TOF-MS: Production of only a compound having a molecular weight of 1705 was confirmed.

IR (film method): (cm$^{-1}$)
3406 ($\nu_{OH}$); 2931 ($\nu_{C-H}$); 1621, 1505, 1436 ($\nu_{C=C\ (aromatic)}$)

$^1$H-NMR (500 MHz, solvent DMSO-d$_6$, internal standard TMS): δ (ppm)=0.86-2.35 (b, 12.0H), 3.98-4.22 (m, 4.0H), 6.09-7.42 (m, 8.0H), 8.65-9.56 (m, 8.0H)

To 40 g of 1-methyl-2-pyrrolidone, 3.5 g of the resulting light yellow solid (S) was added. After further addition of 0.8 g of tetrabutylammonium bromide, the mixture was dissolved by stirring at 70° C. for four hours. After dissolution, 3.3 g of potassium carbonate was added and the mixture was stirred at 70° C. for one hour. Then, a solution of 6.9 g of 2-methyl-2-adamantyl bromoacetate dissolved in 20 g of 1-methyl-2-pyrrolidone was slowly added and the mixture was stirred at 70° C. for six hours. The mixture was cooled to room temperature and extracted using a mixture of water and methylene chloride. The extract was washed three times with 100 ml of 3% aqueous solution of oxalic acid and twice with 100 ml of water. After discharging the water layer, the organic layer was dried using magnesium sulfate and purified by a silica gel column using a 1:4 (volume ratio) mixture of hexane and ethyl acetate as an eluate to obtain 3.2 g of the Compound (A-1).

As a result of $^1$H-NMR analysis, the Compound (A-1) was found to be a compound of the formula (2) in which 40 mol % of the R group was a group shown by the following formula (R-1) (2-methyl-2-adamantyloxycarbonylmethyl group), with the remaining R being hydrogen atoms.

(R-1)

The results of $^1$H-NMR analysis were as follows. $^1$H-NMR (500 MHz, solvent DMSO-d$_6$, internal standard TMS): δ (ppm)=0.82-2.40 (m, 66.4H), 3.80-4.52 (m, 10.4H), 6.08-7.41 (m, 8.0H), 8.62-9.54 (m, 3.2H)

Example 2

Compound (A-2)

To 40 g of 1-methyl-2-pyrrolidone, 3.5 g of the light yellow solid (S) obtained in Example 1 was added. After further addition of 0.8 g of tetrabutylammonium bromide, the mixture was dissolved by stirring at 70° C. for four hours. After dissolution, 3.3 g of potassium carbonate was added and the mixture was stirred at 70° C. for one hour. Then, a solution of 5.6 g of 1-ethylcyclopentyl bromoacetate dissolved in 20 g of 1-methyl-2-pyrrolidone was slowly added and the mixture was stirred at 70° C. for six hours. The mixture was cooled to room temperature and extracted using a mixture of water and methylene chloride. The extract was washed three times with 100 ml of 3% aqueous solution of oxalic acid and twice with 100 ml of water. After discharging the water layer, the organic layer was dried using magnesium sulfate and purified by a silica gel column using a 1:4 (volume ratio) mixture of hexane and ethyl acetate as an eluate to obtain 3.6 g of the Compound (A-2).

As a result of $^1$H-NMR analysis, the Compound (A-2) was found to be a compound of the formula (2) in which 40 mol % of the R group was a group shown by the following formula (R-2) (1-ethylcyclopentyloxycarbonylmethyl group), with the remaining R being hydrogen atoms.

(R-2)

Example 3

Compound (A-3)

In 40 g of 1-methyl-2-pyrrolidone, 3.5 g of the light yellow solid (S) obtained in Example 1 was added and dissolved by stirring at 70° C. for four hours. One gram of a 60% NaH tetrahydrofurane solution was slowly added at 0° C. and the mixture was stirred for 30 minutes. Then, 4.8 g of 2-adamantyl chloromethyl ether was added. The mixture was stirred at room temperature for six hours and extracted with a mixture of water and methylene chloride. Extract was washed twice with 100 ml of water. After discharging the water layer, the organic layer was dried using magnesium sulfate and concentrated under reduced pressure to obtain 3.0 g of the Compound (A-3).

As a result of $^1$H-NMR analysis, the Compound (A-3) was found to be a compound of the formula (2) in which 39 mol % of the R group was a group shown by the following formula (R-3) (2-adamantyloxymethyl group), with the remaining R being hydrogen atoms.

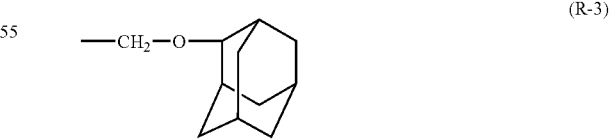

(R-3)

Example 4

Compound (A-4)

To 30 g of 1-methyl-2-pyrrolidone, 5.1 g of the light yellow solid (S) obtained in Example 1 was added. After further addition of 1.1 g of tetrabutylammonium bromide, the mixture was dissolved by stirring at 70° C. for one hour. After dissolution, 5.0 g of potassium carbonate was added and the mixture was stirred at 70° C. for one hour. Then, a solution of 10.8 g of 2-ethyl-2-adamantyl bromoacetate dissolved in 10 g of 1-methyl-2-pyrrolidone was slowly added and the mixture was stirred at 60° C. for six hours. The mixture was cooled to room temperature and extracted using a mixture of water and methylene chloride. The extract was washed three times with 100 ml of 3% aqueous solution of oxalic acid and twice with 100 ml of water. After discharging the water layer, the organic layer was dried using magnesium sulfate and purified by a silica gel column using a 1:4 (volume ratio) mixture of hexane and ethyl acetate as an eluate to obtain 5.1 g of the Compound (A-4).

As a result of $^1$H-NMR analysis, the Compound (A-4) was found to be a compound of the formula (2) in which 40 mol % of the R group was a group shown by the following formula (R-4) (2-ethyl-2-adamantyloxycarbonylmethyl group), with the remaining R being hydrogen atoms.

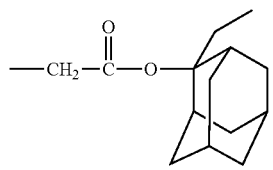

(R-4)

Example 5

Compound (A-8)

To 40 g of 1-methyl-2-pyrrolidone, 3.5 g of the light yellow solid (S) obtained in Example 1 was added. After further addition of 0.8 g of tetrabutylammonium bromide, the mixture was dissolved by stirring at 70° C. for four hours. After dissolution, 3.3 g of potassium carbonate was added and the mixture was stirred at 70° C. for one hour. Then, a solution of 14.2 g of 2-methyl-2-adamantyl bromoacetate dissolved in 20 g of 1-methyl-2-pyrrolidone was slowly added and the mixture was stirred at 70° C. for six hours. The mixture was cooled to room temperature and extracted using a mixture of water and methylene chloride. The extract was washed three times with 100 ml of 3% aqueous solution of oxalic acid and twice with 100 ml of water. After discharging the water layer, the organic layer was dried using magnesium sulfate and purified by a silica gel column using a 1:4 (volume ratio) mixture of hexane and ethyl acetate to obtain 2 g of the Compound (A-8), As a result of $^1$H-NMR analysis, the Compound (A-1) was found to be a compound of the formula (2) in which all the R groups were groups shown by the following formula (R-7) (2-methyl-2-adamantyloxycarbonylmethyl group).

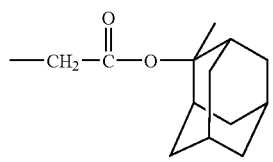

(R-7)

Example 6

Compound (A-9)

In 40 g of 1-methyl-2-pyrrolidone, 3.5 g of the light yellow solid (S) obtained in Example 1 was added and dissolved by stirring at 70° C. for four hours. After the addition of 1.8 g of pyridinium-p-toluenesulfonate, 4.4 g of 2-adamantyl vinyl ether was added dropwise at room temperature. The mixture was stirred at room temperature for 10 hours. After the addition of 2 g of triethylamine, the reaction solution was poured into 600 g of 1% ammonia water to precipitate a solid product, which was dried under reduced pressure to obtain 3.0 g of the Compound (A-9).

As a result of $^1$H-NMR analysis, the Compound (A-9) was found to be a compound of the formula (2) in which 40 mol % of the R group was a group shown by the following formula (R-9) (1-adamantoxymethyl group), with the remaining R being hydrogen atoms.

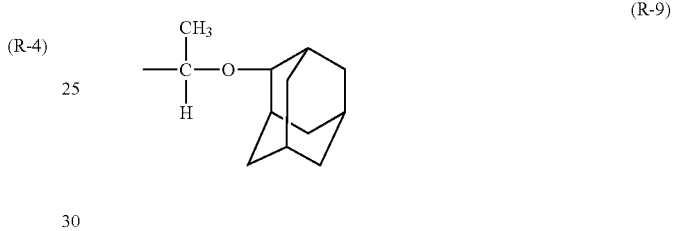

(R-9)

Comparative Synthesis Example 1

Compound (A-5)

In 40 g of 1-methyl-2-pyrrolidone, 3.5 g of the light yellow solid (S) obtained in Example 1 was added and dissolved by stirring at 70° C. for four hours. After the addition of 1.8 g of pyridinium-p-toluenesulfonate, 1.7 g of ethyl vinyl ether was added dropwise at room temperature. The mixture was stirred at room temperature for 10 hours. After the addition of 2 g of triethylamine, the reaction solution was poured into 600 g of 1% ammonia water to precipitate a solid product, which was dried under reduced pressure to obtain 3.0 g of the Compound (A-5).

As a result of $^1$H-NMR analysis, the Compound (A-5) was found to have the following structure (A-5) in which 40 mol % of the R group was a group shown by the following formula (R-5) (1-ethylethyl group), with the remaining R being hydrogen atoms.

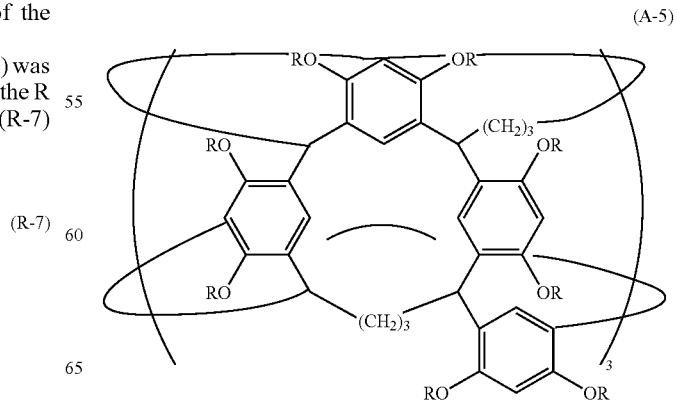

(A-5)

-continued

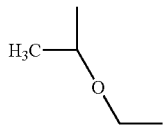
(R-5)

Comparative Synthesis Example 2

Compound (A-6)

To 40 g of 1-methyl-2-pyrrolidone, 3.5 g of the light yellow solid (S) obtained in Example 1 was added. After further addition of 0.8 g of tetrabutylammonium bromide, the mixture was dissolved by stirring at 70° C. for four hours. After dissolution, 3.3 g of potassium carbonate was added and the mixture was stirred at 70° C. for one hour. Then, a solution of 4.7 g of t-butyl bromo acetate dissolved in 20 g of 1-methyl-2-pyrrolidone was slowly added and the mixture was stirred at 70° C. for six hours and, after cooling to room temperature, extracted with a mixture of water and methylene chloride. Extract was washed twice with 100 ml of water. After discharging the water layer, the organic layer was dried using magnesium sulfate and purified by a silica gel column using a 1:4 (volume ratio) mixture of hexane and ethyl acetate as an eluant to obtain 3.8 g of the Compound (A-6).

As a result of $^1$H-NMR analysis, the Compound (A-6) was found to have the following structure (A-6) in which 40 mol % of the R group was a group shown by the following formula (R-6) (tert-butyloxycarbonylmethyl group), with the remaining R being hydrogen atoms.

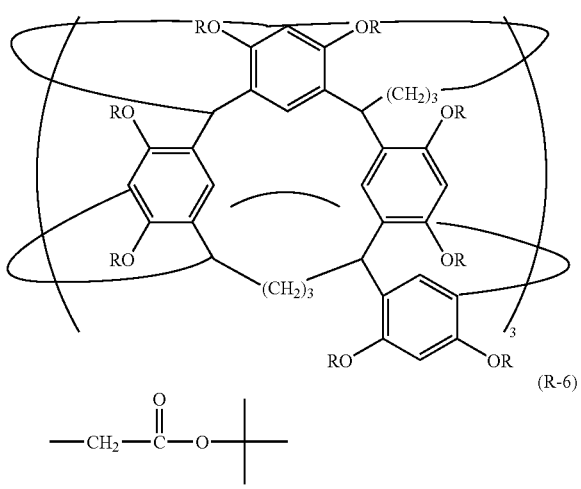

Comparative Synthesis Example 3

Acid-Dissociable Group Containing Resin (A-7)

To a 20% butyl acetate solution of 10 g of polyhydroxystyrene (VP8000 manufactured by Nippon Soda Co., Ltd. (Mw 9000, Mw/Mn=1.1)), 5.50 g of di-t-butyl carbonate and 2.80 g of triethylamine were slowly added dropwise. The mixture was stirred at 60° C. for seven hours. A large amount of water was added to the reaction solution to repeat the precipitation purification. The resulting product was dried under reduced pressure to obtain 12.0 g of acid-dissociable group containing resin (A-7) in which 30% of the hydroxyl groups of the polyhydroxystyrene were protected by t-butyloxycarbonyl.

Example 7

Hundred parts of the Compound (A-1), 9 parts of triphenylsulfonium trifluoromethanesulfonate (shown in Table 1 as "B-1") as a radiation-sensitive acid generator (b), 1 part of tri-n-octylamine (shown in Table 1 as "C-1") as an acid diffusion controller (c), 600 parts of ethyl lactate (shown in Table 1 as "D-1") as a solvent, and 1500 parts of propylene glycol monomethyl ether acetate (shown in Table 1 as "D-3") were mixed. The mixture was filtered through a membrane filter having a pore diameter of 200 nm to obtain a composition solution (radiation-sensitive resin composition). The amount of each component is shown in Table 1.

Each composition solution was then applied onto a silicon wafer using a spin coater and was pre-baked for 90 seconds at 130° C. in a clean track (ACT-8 manufactured by Tokyo Electron, Ltd.) to form a resist (radiation-sensitive composition) film with a thickness of 100 nm. The resist film was irradiated with an electron beam using a simplified electron beam writer (HL800D manufactured by Hitachi, Ltd., output: 50 KeV, current density: 5.0 A/cm$^2$). After exposure to the electron beam, the resist film was baked (PEB) at 130° C. for 90 seconds. A resist pattern was obtained by developing the resist at 23° C. for 1 minute by a paddle method using a 2.38% tetramethylammonium hydroxide aqueous solution, followed by washing with purified water and drying. Evaluation of resists was carried out as follows. The evaluation results are shown in Table 3.

Figure 2:
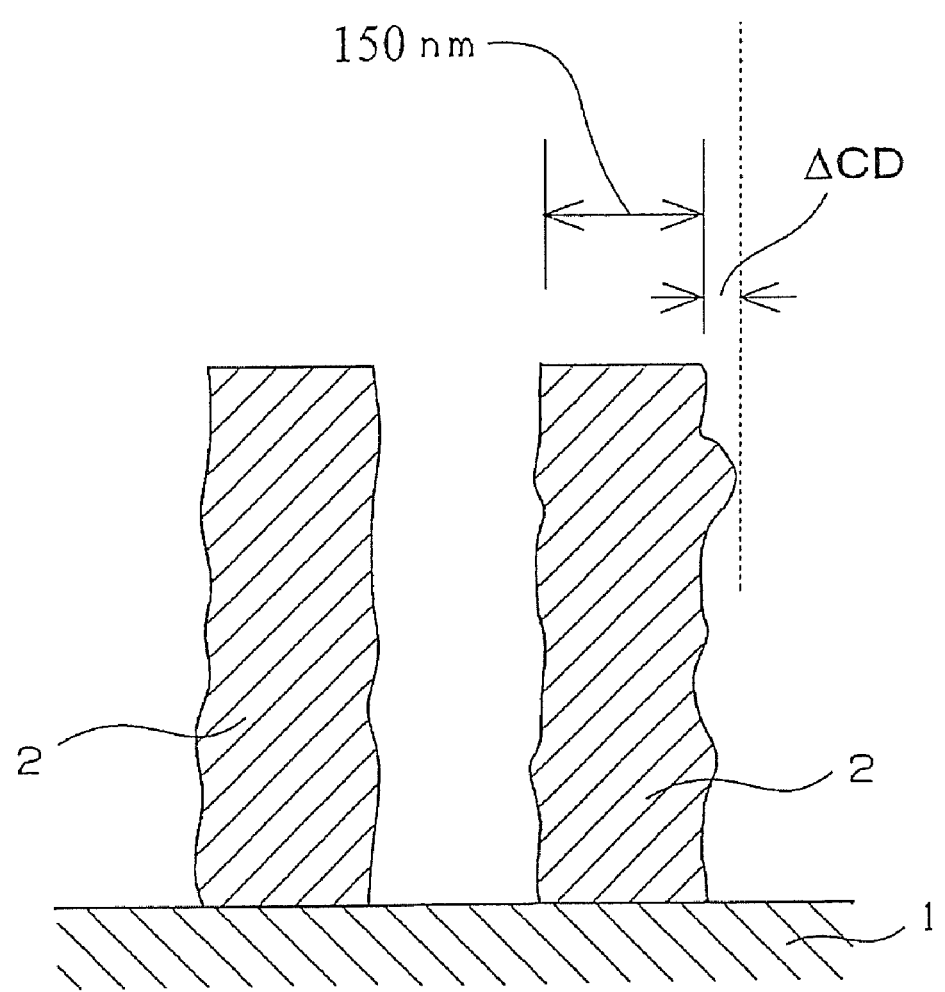
FIG. 2 is a cross-sectional view schematically showing a line- and space pattern.

(1) Sensitivity (L/S):

A resist pattern was formed by irradiating the resist film formed on a silicon wafer, followed by immediate post exposure baking (PEB), alkali development, washing with water, and drying. An exposure dose capable of forming a line-and-space pattern (1L1S), which consists of a line part with a width of 150 nm and a space part (groove) with an interval of 150 nm between two adjacent line parts, into a 1:1 line width is defined as an optimum exposure dose. The sensitivity was evaluated by the optimum exposure dose. FIG. 1 is a plan view schematically showing the line-and-space pattern. FIG. 2 is a cross-sectional view schematically showing a line- and space pattern. Irregularities in FIGS. 1 and 2 are exaggerated.

(2) Resolution (L/S):

In the line-and-space (1L1S) pattern, the minimum line width (nm) of line pattern (line part) resolved by the optimum exposure dose dimension was taken as the resolution.

(3) Nano Edge Roughness:

The line-and-space (1L1S) line pattern with a line width of 150 nm was inspected using a scanning electron microscope for semiconductors (high-resolution FEB measurement device "S-9220" manufactured by Hitachi, Ltd.). Using the configurations observed in Examples as shown in FIGS. 1 and 2, the difference "ΔCD" of the line width and the designed line width of 150 nm at a point at which the irregularities produced along the horizontal side 2a in the line part 2 of the resist film formed on silicon wafer 1 was most conspicuous was measured using a CD-SEM ("S-9220" manufactured by Hitachi High-Technologies Corporation).

As a result of evaluation in Examples, the sensitivity was 17.0 μC/cm$^2$, resolution was 80 nm, and nano edge roughness was 8 nm.

Examples 8 to 26 and Comparative Examples 1 to 3

The composition solutions were prepared in the same manner as in Example 7, except that the components shown in Tables 1 and 2 were mixed and treated under the conditions shown in Table 3 to prepare homogeneous solutions. The resist patterns were formed using the radiation-sensitive compositions to evaluate the above properties. The evaluation results are shown in Table 3.

TABLE 1

| | Compound (a) | | Radiation-sensitive acid generator (b) | | | | Acid diffusion controller (c) | | | | Solvent | | | |
|---|---|---|---|---|---|---|---|---|---|---|---|---|---|---|
| | Type | Amount (Part) | Type | Amount (Part) | Type | Amount (Part) | Type | Amount (Part) | Type | Amount (Part) | Type | Amount (Part) | Type | Amount (Part) |
| Example 7 | A-1 | 100 | B-1 | 9 | — | — | C-1 | 1 | — | — | D-1 | 600 | D-3 | 1500 |
| Example 8 | A-1 | 100 | B-1 | 9 | — | — | C-2 | 1.5 | — | — | D-1 | 600 | D-3 | 1500 |
| Example 9 | A-1 | 100 | B-2 | 9 | — | — | C-3 | 0.9 | — | — | D-1 | 600 | D-3 | 1500 |
| Example 10 | A-2 | 100 | B-1 | 9 | — | — | C-1 | 1 | — | — | D-1 | 600 | D-3 | 1500 |
| Example 11 | A-3 | 100 | B-1 | 9 | — | — | C-1 | 1 | — | — | D-1 | 600 | D-3 | 1500 |
| Example 12 | A-1 | 100 | B-1 | 9 | B-3 | 2 | C-1 | 1 | C-4 | 0.2 | D-1 | 600 | D-2 | 1500 |
| Example 13 | A-3 | 100 | B-4 | 9 | — | — | C-2 | 1.5 | — | — | D-1 | 600 | D-3 | 1500 |
| Example 14 | A-3 | 100 | B-4 | 9 | — | — | C-1 | 1 | — | — | D-1 | 600 | D-3 | 1500 |
| Example 15 | A-1 | 100 | B-1 | 9 | B-5 | 1 | C-3 | 0.2 | — | — | D-1 | 600 | D-2 | 1500 |
| Example 16 | A-1 | 100 | B-1 | 9 | B-6 | 3 | C-2 | 1.5 | — | — | D-1 | 600 | D-3 | 1500 |
| Example 17 | A-1 | 100 | B-1 | 9 | B-7 | 3 | C-2 | 1.5 | — | — | D-1 | 600 | D-3 | 1500 |
| Example 18 | A-1 | 100 | B-1 | 9 | — | — | C-5 | 0.9 | — | — | D-1 | 600 | D-3 | 1500 |
| Example 19 | A-1 | 100 | B-1 | 9 | — | — | C-6 | 0.9 | — | — | D-1 | 600 | D-3 | 1500 |
| Example 20 | A-1 | 100 | B-8 | 9 | — | — | C-5 | 0.9 | — | — | D-1 | 600 | D-3 | 1500 |
| Example 21 | A-1 | 100 | B-9 | 9 | — | — | C-5 | 0.9 | — | — | D-1 | 600 | D-3 | 1500 |
| Example 22 | A-1 | 100 | B-1 | 9 | — | — | C-2 | 1 | C-5 | 0.2 | D-1 | 600 | D-3 | 1500 |
| Example 23 | A-1 | 100 | B-1 | 9 | — | — | C-2 | 1.5 | — | — | D-1 | 600 | D-3 | 1500 |
| Example 24 | A-4 | 100 | B-1 | 9 | — | — | C-2 | 1.5 | — | — | D-1 | 600 | D-3 | 1500 |
| Example 25 | A-8 | 100 | B-1 | 9 | — | — | C-1 | 1 | — | — | D-1 | 600 | D-3 | 1500 |
| Example 26 | A9 | 100 | B-1 | 9 | — | — | C-1 | 1 | — | — | D-1 | 600 | D-3 | 1500 |

TABLE 2

| | Compound (a) | | Radiation-sensitive acid generator (b) | | | | Acid diffusion controller (c) | | | | Solvent | | | |
|---|---|---|---|---|---|---|---|---|---|---|---|---|---|---|
| | Type | Amount (Part) | Type | Amount (Part) | Type | Amount (Part) | Type | Amount (Part) | Type | Amount (Part) | Type | Amount (Part) | Type | Amount (Part) |
| Comparative Example 1 | A-5 | 100 | B-1 | 9 | — | — | C-1 | 1 | — | — | D-1 | 600 | D-3 | 1500 |
| Comparative Example 2 | A-6 | 100 | B-1 | 9 | — | — | C-1 | 1 | — | — | D-1 | 600 | D-3 | 1500 |
| Comparative Example 3 | A-7 | 100 | B-1 | 9 | — | — | C-1 | 1 | — | — | D-1 | 600 | D-3 | 1500 |

TABLE 3

| | PB conditions | | PEB conditions | | | | |
|---|---|---|---|---|---|---|---|
| | Temperature (° C.) | Time (sec) | Temperature (° C.) | Time (sec) | Sensitivity (μC/cm$^2$) | Resolution | Nano-edge roughness |
| Example 7 | 130 | 90 | 130 | 90 | 17.0 | 80 nm | 8 nm |
| Example 8 | 130 | 90 | 130 | 90 | 16.0 | 80 nm | 7 nm |
| Example 9 | 130 | 90 | 130 | 90 | 18.0 | 90 nm | 8 nm |
| Example 10 | 130 | 90 | 130 | 90 | 18.0 | 80 nm | 8 nm |

TABLE 3-continued

|  | PB conditions | | PEB conditions | | Sensitivity ($\mu C/cm^2$) | Resolution | Nano-edge roughness |
| --- | --- | --- | --- | --- | --- | --- | --- |
|  | Temperature (°C.) | Time (sec) | Temperature (°C.) | Time (sec) |  |  |  |
| Example 11 | 110 | 90 | 110 | 90 | 19.0 | 90 nm | 9 nm |
| Example 12 | 130 | 90 | 130 | 90 | 18.0 | 90 nm | 8 nm |
| Example 13 | 110 | 90 | 110 | 90 | 17.0 | 90 nm | 9 nm |
| Example 14 | 110 | 90 | 110 | 90 | 17.0 | 90 nm | 8 nm |
| Example 15 | 130 | 90 | 120 | 90 | 18.0 | 90 nm | 9 nm |
| Example 16 | 130 | 90 | 130 | 90 | 16.0 | 80 nm | 6 nm |
| Example 17 | 130 | 90 | 130 | 90 | 16.0 | 80 nm | 6 nm |
| Example 18 | 130 | 90 | 130 | 90 | 16.0 | 80 nm | 7 nm |
| Example 19 | 130 | 90 | 130 | 90 | 16.0 | 80 nm | 7 nm |
| Example 20 | 130 | 90 | 130 | 90 | 17.0 | 80 nm | 8 nm |
| Example 21 | 130 | 90 | 130 | 90 | 17.0 | 80 nm | 8 nm |
| Example 22 | 130 | 90 | 130 | 90 | 16.0 | 80 nm | 7 nm |
| Example 23 | 140 | 90 | 90 | 90 | 17.0 | 80 nm | 7 nm |
| Example 24 | 140 | 90 | 90 | 90 | 15.0 | 80 nm | 6 nm |
| Example 25 | 130 | 90 | 130 | 90 | 20.0 | 90 nm | 10 nm |
| Example 26 | 110 | 90 | 110 | 90 | 14 | 80 nm | 6 nm |
| Comparative Example 1 | 110 | 90 | 110 | 90 | 22.0 | 110 nm | 13 nm |
| Comparative Example 2 | 110 | 90 | 110 | 90 | 23.0 | 100 nm | 12 nm |
| Comparative Example 3 | 90 | 90 | 90 | 90 | 25.0 | 100 nm | 12 nm |

The materials used in Examples 7 to 26 and Comparative Examples 1 to 3 are as follows.
(b) Radiation-Sensitive Acid Generator:
B-1: Triphenylsulfonium trifluoromethanesulfonate
B-2: N-(Trifluoromethylsulfonyloxy)bicyclo[2.2.1]hept-5-ene-2,3-dicarboxylmide
B-3: 2,4,6-Trimethylphenyldiphenylsulfonium-4-trifluoromethylbe nzenesulfonate
B-4: Triphenylsulfonium n-octanesulfonate
B-5: Diphenyliodonium trifluoromethanesulfonate
B-6: Triphenylsulfonium 1,1,2,2-tetrafluoro-2-(tetracyclo[4.4.0.1$^{2,5}$.1$^{7,10}$] dodecan-8-yl)ethanesulfonate
B-7: Triphenylsulfonium 1,1-difluoro-2-(bicyclo[2.2.1]heptan-2-yl)ethanesulfonate
B-8: 2,4,6-Trimethylphenyldiphenylsulfonium-2,4-difluorobenzene sulfonate
(c) Acid Diffusion Controller:
C-1: Tri-n-octylamine
C-2: Triphenylsulfonium salicylate
C-3: N-t-Butoxycarbonyldicyclohexylamine
C-4: 4-Phenylpyridine
(C-5): (R)-(+)-1-(t-Butoxycarbonyl)-2-pyrrolidinemethanol
(C-6): (S)-(−)-1-(t-Butoxycarbonyl)-2-pyrrolidinemethanol
Solvents:
D-1: Ethyl 2-hydroxypropionate
D-2: Ethyl 3-ethoxypropionate
D-3: Propylene glycol monomethyl ether acetate As clearly shown in Table 3, the radiation-sensitive compositions of Examples 7 to 26 which contain any one of the compounds of Examples 1 to 6 were confirmed to be able to form a chemically-amplified positive-tone resist film which effectively responds to electron beams or extreme ultraviolet radiation, exhibits only low roughness, excels in etching resistance and sensitivity, and can form high precision minute patterns in a stable manner, as compared with the radiation-sensitive compositions of Comparative Examples 1 to 3 which contain any one of the compounds of Comparative Synthesis Example 1 or 2, or the resin of Comparative Synthesis Example 3.

INDUSTRIAL APPLICABILITY

The compound of the present invention can be suitably used in the field of microfabrication represented by the manufacturing of integral circuit elements. When the compound is used in preparing a radiation-sensitive composition, the resulting composition can suitably form a chemically-amplified positive tone resist for the manufacture of semiconductor devices.

The radiation-sensitive composition of the present invention not only excels in resolution of the line-and-space pattern when forming a pattern, but also produces a minimal nano edge roughness. Therefore, the composition is useful for forming micropatterns using EB, EUV, and X rays. The composition therefore can be extremely useful as a material for forming a chemically-amplified resist film for manufacturing semiconductor devices, which will become more and more miniaturized in the future.

The invention claimed is:
1. A compound shown by the following formula (1),

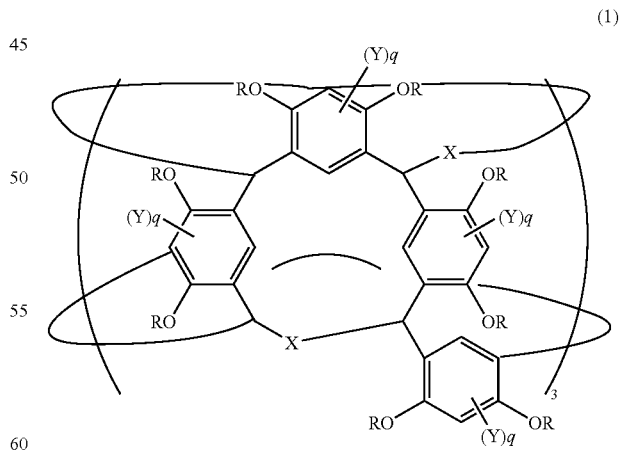

(1)

wherein Rs individually represent a hydrogen atom or an acid-dissociable group having a substituted or unsubstituted cyclic structure, provided that at least one of the Rs is an acid-dissociable group having a substituted or unsubstituted cyclic structure; Xs individually represent a substituted or unsubstituted alkylene group having 1 to 8 carbon atoms; Ys individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group; and qs are individually 0 or 1, and wherein the acid-dissociable group is a group shown by the following formula (2-1) or (2-2), (2-1)
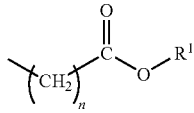

(2-2)
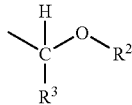

wherein, in the formula (2-1), $R^1$ represents a substituted or unsubstituted cycloalkyl group having 6 to 20 carbon atoms which may contain a hetero atom and n is an integer of 1 to 3, and in the formula (2-2), $R^2$ represents a substituted or unsubstituted cycloalkyl group having 6 to 20 carbon atoms which may contain a hetero atom and $R^3$ represents a hydrogen atom or an alkyl group having 1 to 5 carbon atoms.

2. The compound according to claim 1 which is shown by the following formula (2), (2)
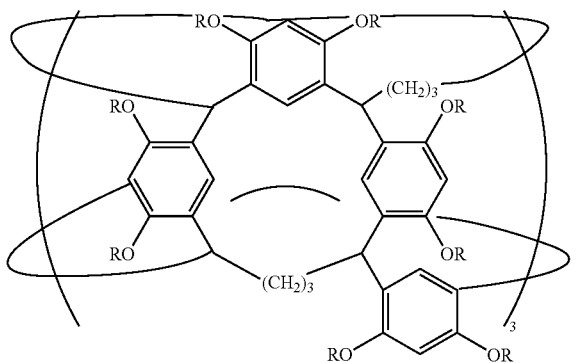

wherein Rs individually represent a hydrogen atom or the acid-dissociable group, provided that at least one of the Rs is the acid-dissociable group.

3. The compound according to claim 2, wherein $R^1$ in the formula (2-1) is a 2-methyl-2-adamantyl group, a 2-ethyl-2-adamantyl group, a 1-ethylcyclopentyl group, or a 1-methylcyclopentyl group, R in the formula (2-2) is an adamantyl group, a 2-ethyl-2-adamantyl group, or a 2-methyl-2-adamantyl group, and $R^3$ is a hydrogen atom or a methyl group.

4. A radiation-sensitive composition comprising (a) a compound according to claim 2, and (b) a radiation-sensitive acid generator which generates an acid upon exposure to radiation.

5. The radiation-sensitive composition according to claim 4, wherein the radiation-sensitive acid generator (b) is at least one compound selected from the group consisting of an onium salt, a diazomethane compound, and a sulfonimide compound.

6. The radiation-sensitive composition according to claim 4, further comprising an acid diffusion controller (c).

7. The compound according to claim 1, wherein $R^1$ in the formula (2-1) is a 2-methyl-2-adamantyl group, a 2-ethyl-2-adamantyl group, a 1-ethylcyclopentyl group, or a 1-methylcyclopentyl group, R in the formula (2-2) is an adamantyl group, a 2-ethyl-2-adamantyl group, or a 2-methyl-2-adamantyl group, and $R^3$ is a hydrogen atom or a methyl group.

8. A radiation-sensitive composition comprising (a) a compound according to claim 1, and (b) a radiation-sensitive acid generator which generates an acid upon exposure to radiation.

9. The radiation-sensitive composition according to claim 8, wherein the radiation-sensitive acid generator (b) is at least one compound selected from the group consisting of an onium salt, a diazomethane compound, and a sulfonimide compound.

10. The radiation-sensitive composition according to claim 8, further comprising an acid diffusion controller (c).

* * * * *